United States Patent
Durst et al.

(10) Patent No.: US 7,419,796 B2
(45) Date of Patent: Sep. 2, 2008

(54) METHOD OF MAKING A TEST DEVICE

(75) Inventors: Richard A. Durst, Romulus, NY (US); Daniel Martorell-Pena, Barcelona (ES); Sui Ti Atienza Siebert, Geneva, NY (US)

(73) Assignee: Cornell Research Foundation, Ithaca, NY (US)

( * ) Notice: Subject to any disclaimer, the term of this patent is extended or adjusted under 35 U.S.C. 154(b) by 619 days.

(21) Appl. No.: 10/264,159

(22) Filed: Oct. 2, 2002

(65) Prior Publication Data

US 2003/0104506 A1 Jun. 5, 2003

Related U.S. Application Data

(63) Continuation of application No. 09/603,126, filed on Jun. 23, 2000, now abandoned.

(60) Provisional application No. 60/140,572, filed on Jun. 23, 1999.

(51) Int. Cl.
*G01N 33/53* (2006.01)

(52) U.S. Cl. .................. 435/7.92; 436/518; 436/532; 436/829; 424/9.321

(58) Field of Classification Search ............. 436/518, 436/532, 829, 810; 424/9.321
See application file for complete search history.

(56) References Cited

U.S. PATENT DOCUMENTS

| | | | |
|---|---|---|---|
| 4,048,298 A | 9/1977 | Niswender | |
| 4,172,770 A | 10/1979 | Semersky et al. | |
| 4,225,410 A | 9/1980 | Pace | |
| 4,235,601 A | 11/1980 | Deutsch et al. | |
| 4,517,288 A | 5/1985 | Giegel et al. | |
| 4,517,303 A | 5/1985 | Freytag et al. | |
| 4,571,543 A | 2/1986 | Raymond et al. | |
| 4,594,327 A | 6/1986 | Zuk | |
| 4,605,630 A | 8/1986 | Kung et al. | |
| 4,636,479 A | 1/1987 | Martin et al. | |
| 4,668,619 A | 5/1987 | Greenquist et al. | |
| 4,695,554 A | 9/1987 | O'Connell et al. | |
| 4,703,017 A | 10/1987 | Campbell et al. | |
| 4,708,933 A | 11/1987 | Huang et al. | |
| 4,752,572 A | 6/1988 | Sundberg et al. | |
| 4,806,311 A | 2/1989 | Greenquist | |
| 4,822,566 A | 4/1989 | Newman | |
| 4,855,240 A | 8/1989 | Rosenstein et al. | |
| 4,874,710 A | 10/1989 | Piran | |
| 4,880,635 A | 11/1989 | Janoff et al. | |
| 4,916,080 A | 4/1990 | Imai et al. | |
| 4,920,046 A | 4/1990 | McFarland et al. | |
| 4,931,385 A * | 6/1990 | Block et al. ............. | 435/7.94 |
| 4,939,098 A | 7/1990 | Suzuki et al. | |
| 5,001,048 A | 3/1991 | Taylor et al. | |
| 5,006,473 A | 4/1991 | Bouma et al. | |
| 5,045,285 A | 9/1991 | Kolesar, Jr. | |
| 5,047,245 A | 9/1991 | Bally et al. | |
| 5,081,013 A | 1/1992 | Rovelli et al. | |
| 5,085,987 A | 2/1992 | Olson | |
| 5,089,181 A | 2/1992 | Hauser | |
| 5,096,629 A | 3/1992 | Nanba et al. | |
| 5,130,257 A | 7/1992 | Baer et al. | |
| 5,141,751 A | 8/1992 | Tomikawa et al. | |
| 5,141,868 A | 8/1992 | Shanks et al. | |
| 5,155,022 A | 10/1992 | Naqui et al. | |
| 5,169,789 A | 12/1992 | Bernstein | |
| 5,173,406 A | 12/1992 | Hosoda et al. | |
| 5,194,133 A | 3/1993 | Clark et al. | |
| 5,198,367 A | 3/1993 | Aizawa et al. | |
| 5,200,051 A | 4/1993 | Cozzette et al. | |
| 5,208,143 A | 5/1993 | Henderson et al. | |
| 5,248,590 A | 9/1993 | Rutner et al. | |

(Continued)

FOREIGN PATENT DOCUMENTS

EP           0 291 194      *    4/1988

(Continued)

OTHER PUBLICATIONS

Madden et al., "Protection of Large Unilamellar Vesicles by Trehalose During Dehydration: Retention of Vesicle Contents," *Biochim. et Biophys. Acta*, 817:67-74 (1985).
Crowe et al., "Preservation of Freeze-Dried Liposomes by Trehalose," *Archives of Biochem. and Biophys.*, 242:240-247 (1985).
Harrigan et al., "Protection of Liposomes During Dehydration or Freezing," *Chemistry and Physics of Lipids*, 52:139-149 (1990).
Crowe et al., "Preservation of Liposomes by Freeze-Drying," in *Liposome Technology*, Gregoriadis, ed., CRC Press, Boca Raton, pp. 229-252 (1993).
Ausborn et al., "The Protective Effect of Free and Membrane-Bound Cryoprotectants During Freezing and Freeze-Drying of Liposomes," *J. of Controlled Release*, 30:105-116 (1994).
Martorell et al., "Liposome Dehydration on Nitrocellulose and Its Application in a Biotin Immunoassay", *Analytical Biochemistry*, 271:177-185 (1999).

(Continued)

*Primary Examiner*—Bao-Thuy L Nguyen
(74) *Attorney, Agent, or Firm*—Nixon Peabody LLP

(57) ABSTRACT

The present invention relates to a method for making a test device for detecting or quantifying an analyte in a sample. This method involves contacting a membrane with a mixture including derivatized, marker-loaded liposomes, and substantially dehydrating the mixture on the membrane under vacuum pressure at a temperature of from about 4° C. to about 80° C., wherein said mixture further includes one or more sugars in an amount sufficient to promote the stability of the liposomes during dehydration and rehydration. The present invention also relates to a test device and method for detecting or quantifying an analyte in a sample. The test device includes a membrane which includes an immobilized liposome zone, wherein the immobilized liposome zone has bound thereto dehydrated, derivatized, marker-loaded liposomes dehydrated under vacuum pressure at a temperature of from about 4° C. to about 80° C. from a mixture which includes one or more sugars in an amount sufficient to promote the stability of the liposomes during dehydration and rehydration.

15 Claims, 8 Drawing Sheets

U.S. PATENT DOCUMENTS

| | | | |
|---|---|---|---|
| 5,308,775 | A | 5/1994 | Donovan et al. |
| 5,310,650 | A | 5/1994 | McMahon et al. |
| 5,312,762 | A | 5/1994 | Guiseppi-Elie |
| 5,340,716 | A | 8/1994 | Ullman et al. |
| 5,346,832 | A | 9/1994 | Aizawa et al. |
| 5,354,692 | A | 10/1994 | Yang et al. |
| 5,369,036 | A | 11/1994 | Mercolino et al. |
| 5,384,264 | A | 1/1995 | Chen et al. |
| 5,389,523 | A | 2/1995 | Plant et al. |
| 5,393,527 | A | 2/1995 | Malick et al. |
| 5,399,500 | A | 3/1995 | Oppenheimer et al. |
| 5,416,214 | A | 5/1995 | Pease et al. |
| 5,459,041 | A | 10/1995 | Blaser et al. |
| 5,491,097 | A | 2/1996 | Ribi et al. |
| 5,494,803 | A | 2/1996 | Carbonell et al. |
| 5,498,551 | A | 3/1996 | De Jaegar et al. |
| 5,516,638 | A | 5/1996 | Urnovitz et al. |
| 5,529,902 | A | 6/1996 | Kottke et al. |
| 5,532,133 | A | 7/1996 | Barnwell |
| 5,567,591 | A | 10/1996 | Lovell et al. |
| 5,591,645 | A | 1/1997 | Rosenstein |
| 5,635,357 | A | 6/1997 | Malick et al. |
| 5,665,552 | A | 9/1997 | Maret et al. |
| 5,670,328 | A | 9/1997 | Inoue et al. |
| 5,672,478 | A | 9/1997 | Singh et al. |
| 5,712,170 | A | 1/1998 | Kouvonen et al. |
| 5,738,868 | A | 4/1998 | Shinkarenko |
| 5,753,519 | A | 5/1998 | Durst et al. |
| 5,756,362 | A | 5/1998 | Durst et al. |
| 5,756,879 | A | 5/1998 | Yamagishi et al. |
| 5,766,961 | A | 6/1998 | Pawlak et al. |
| 5,769,080 | A | 6/1998 | Unger et al. |
| 5,770,460 | A | 6/1998 | Pawlak et al. |
| 5,776,487 | A | 7/1998 | Maxfield Wilson et al. |
| 5,780,010 | A | 7/1998 | Lanza et al. |
| 5,789,154 | A | 8/1998 | Durst et al. |
| 5,817,334 | A | 10/1998 | Schmidt et al. |
| 5,863,538 | A | 1/1999 | Thorpe et al. |
| 5,922,350 | A * | 7/1999 | Janoff et al. ............... 424/450 |
| 5,948,624 | A | 9/1999 | Rothschild |
| 5,958,791 | A | 9/1999 | Roberts et al. |
| 6,004,442 | A | 12/1999 | Choulga et al. |
| 6,040,195 | A | 3/2000 | Carroll et al. |
| 6,086,748 | A | 7/2000 | Durst et al. |
| 6,103,127 | A | 8/2000 | Pourfarzaneh |
| 6,159,745 | A | 12/2000 | Roberts et al. |
| 6,248,596 | B1 | 6/2001 | Durst et al. |
| 6,261,535 | B1 | 7/2001 | Thorpe et al. |
| 6,358,752 | B1 | 3/2002 | Durst et al. |
| 6,395,517 | B1 | 5/2002 | Abbaszadegan et al. |
| 6,576,460 | B1 | 6/2003 | Baeumner et al. |
| 2002/0102581 | A1 | 8/2002 | Hageman et al. |
| 2003/0162198 | A1 | 8/2003 | Rothschild et al. |

FOREIGN PATENT DOCUMENTS

| | | |
|---|---|---|
| EP | 0 276 165 | 7/1988 |
| EP | 0 387 696 A2 | 9/1990 |
| EP | 0 402 917 B1 | 12/1990 |
| EP | 0 437 092 A1 | 7/1991 |
| GB | 2204398 | 11/1988 |
| JP | 2308800 | 12/1990 |
| JP | 3267000 | 11/1991 |
| JP | P4135497 | 5/1992 |
| JP | P4286957 | 10/1992 |
| WO | WO 88/04431 | 6/1988 |
| WO | WO 90/02334 | 3/1990 |
| WO | WO 94/03809 | 2/1994 |
| WO | WO 96/24062 | 8/1996 |
| WO | WO 98/36736 | 8/1998 |
| WO | WO 99/60399 | 11/1999 |
| WO | WO 00/72019 | 11/2000 |
| WO | WO 00/79283 | 12/2000 |

OTHER PUBLICATIONS

Durst, "Automated Analyzer for the Determination of Potassium and Sodium in Whole Blood," *Clinica Chimica Acta*, 80:225-234 (1977).

Durst et al., "Organic Electrochemical Techniques Having Potential Clinical Application," *Clinical Chemistry*, 28:1922-1930 (1982).

Zuk et al., "Enzyme Immunochromatography-A Quantitative Immunoassay Requiring No Instrumentation," *Clin. Chem.*, 31(7):1144-50 (1985).

Heath-Fracica et al., "Evaluation of a New Latex Agglutination Test for Detection of Streptococcal Antibodies," *Diagn. Microbiol. Infect. Dis.*, 8:25-30 (1987).

Murray et al., "Chemically Modified Electrodes Molecular Design for Electroanalysis," *Analytical Chemistry*, 59:379A-390A (1987).

Kannuck et al., "Measurement of Liposome-Released Ferrocyanide by a Dual-Function Polymer Modified Electrode," *Anal. Chemistry*, 60:142-147 (1988).

Durst et al., "Chemically Modified Electrode for Liposome-Mediated Homogeneous Immunoassay," 5th Symposium on Ion-Selective Electrodes, *Pergamon Press*, Oxford (1989).

Monroe, "Novel Liposome Immunoassays for Detecting Antigens, Antibodies and Haptens," *J. Liposome Res.*, 1:339-337 (1989-1990).

Plant et al., "Generic Liposome Reagent for Immunoassays," *Anal. Biochem.*, 176:420-426 (1989).

Allen et al., "A Noninstrumented Quantitive Test System and Its Application for Determining Cholesterol Concentration in Whole Blood," *Clin. Chem.*, 36:1591-1597 (1990).

Durst et al., "Automated Liposome-Based Flow Injection Immunoassay System," GBF (Gesellschaft für Biotechnologische Forschung) Monographs, 14:181-190 (1990).

Locascio-Brown et al., "Liposome flow Injection Immunoassay: Implications for Sensitivity, Dynamic Range, and Antibody Regeneration," *Analytical Chemistry*, 2587-93 (1990).

Collard-Bovy et al., "Microparticle-Enhanced Nephelometric Immunoassay. 1. Measurement of $\alpha_s$-Casein and $\alpha$-Casein," *J. Dairy Sci.*, 74:3695-3701 (1991).

Yap et al., "Liposome Flow Injection Immunoassay: Model Calculations of Competitive Immunorections Involving Univalent and Multivalent Ligands," *Analytical Chemistry*, 63:2007-11 (1991).

Armbruster et al., "Screening for Drugs of Abuse with the Roche ONTRAK Assays," *J. Anal. Tax.*, 16:172-175 (1992).

Durst et al., "Development of Liposome-Enhanced Immuno-Biosensing Devices for Field Measurements of Toxic Substances," *2nd Bioelectroanalytical Symposium, Mátrafüred*, 1992, Akadémiai Kiadó, Budapest.

Pinnaduwage et al., "Stable Target-Sensitive Immunoliposomes," *Biochemistry*, 31:2850-2855 (1992).

Babbitt et al., "Contact-Dependent, Immunecomplex-Mediated Lysis of Hapten-Sensitized Liposomes," *Bioconjugat Chem.*, 4:199-205 (1993).

Durst et al., "Immunosensor for Extra-Lab Measurements Based on Liposome Amplification and Capillary Migration," *Biosensors & Bioelectronics*, 8:xiii-xv (1993).

Losso et al., "Development of a Particle Concentration Fluorescence Immunoassay for the Quantitative Determination of IgG in Bovine Milk," *J. Agric. Food Chem.*, 41:682-686 (1993).

Lou et al., "One-Step Competitive Immunochromatographic Assay for Semiquantitative Determination of Lipoprotein(a) in Plasma," *Clin. Chem.*, 39:619-624 (1993).

Parsons et al., "Multianalyte Assay System Developed for Drugs of Abuse," *Clin. Chem.*, 39:1899-1903 (1993).

Rosenzweig et al., "Laser-Based Particle-Counting Microimmunoassay for the Analysis of Single Human Erythrocytes," *Anal. Chem.*, 66:1771-1776 (1994).

Reeves et al., "Novel Optical Measurement Approach for the Quantitation of Liposome Immunomigration Assays," *Analytical Letters*, 28:2347-2352 (1995).

Roberts et al., "Investigation of Liposome-Based Immunomigration Sensors for the Detection of Polychlorinated Biphenyls," *Analytical Chemistry*, 67:482-491 (1995).

Siebert et al., "Liposome Immunomigration Field Assay Device for Alachlor Determination," *Analytica Chimica Acta* 282:297-305 (1993).

Niwa et al., "Electrochemical Behavior of Reversible Redox Species at Interdigitated Array Electrodes with Different Geometries: Consideration of Redox Cycling and Collection Efficiency," *Anal. Chem.*, 62:447:452 (1990).

Niwa et al., "Small-Volume Voltammetric Detection of 4-Aminophenol with Interdigitated Array Electrodes and Its Application to Electrochemical Enzyme Immunoassay," *Anal. Chem.*, 65:1559-1563 (1993).

Rule et al., "Rapid Method for Visual Identification or Specific DNA Sequences Based on DNA-Tagged Liposomes," *Clin. Chem.*, 42(8):1206-1209 (1996).

Rule et al., "Characteristics of DNA-Tagged Liposomes Allowing Their Use in Capillary-Migration, Sandwich-Hybridization Assays," *Anal. Biochem.*, 244:260-269 (1997).

Durst, "Development of a Liposome-Enhanced Assay Format for the Detection of Specific Nucleic Acid Sequences," Cornell Center for Advanced Technology (CAT)—Biotechnology Program, Research Directory (1994-1995) (abstract).

Umeda et al., "Liposome Immune Lysis Assay (LILA). Application of Sandwich Method to Determine a Serum Protein Component With Antibody-Bearing, Liposomes," *J. Immunol. Methods*, 95:15-21 (1986).

Umeda et al., "A Novel Liposome Immune Lysis Assay (LILA) for Determination of CRP Antigen Using Two Monoclonal Antibodies Recognizing Different Antigenic Determinants," *Acta Med. Okayama*, 48(6):299-304 (1994).

Ho et al., "Interactions of Target-Sensitive Immunoliposomes with Herpes Simplex Virus," *J. Biol. Chem.*, 262(29):13979-13984 (1987).

Singh et al., "Application of Antibody and Fluorophore-Derivatized Liposomes to Heterogeneous Immunoassays for D-dimer," *Biotechnol. Prog.*, 12:272-280 (1996).

Kung et al., "Large Liposome Agglutinaton Technique for the Serological Detection of Syphilis," *J. Immunol. Methods*, 90:189-196 (1986).

Price et al., "Development of a Simple and Rapid Universal RNA Biosensor," NIH-BECON Conference (May 31-Jun. 4, 2002).

Price et al., "Development of a Simple and Rapid Universal RNA Biosensor," NIH-BECON Conference (May 31-Jun. 4, 2002) (abstract).

Min et al., "Characteristics of Interdigitated Ultramicroelectrode Arrays as Electrochemical Biosensor Transducers," *Biology & Chemistry*, NNUN Abstracts 2002 pp. 7.

Moussa et al., "Development of Ultramicroelectrode Arrays for Microfluidic Biosensor Devices," The 2001 NNUN REV Research Accomplishments (Nov. 28, 2001).

Moussa et al., "Development of Ultramicroelectrode Arrays for Microfluidic Biosensor Devices," NNUN Abstracts 2002 pp. 24-25 (Mar. 19, 2002).

* cited by examiner

METHOD OF MAKING A TEST DEVICE

This application is a continuation of U.S. patent application Ser. No. 09/603,126 filed Jun. 23, 2000 now abandoned, which claims the benefit of U.S. Provisional Patent Application Ser. No. 60/140,572, filed Jun. 23, 1999, which is hereby incorporated by reference.

FIELD OF THE INVENTION

The present invention relates to a method of making a test device which includes dehydrated, derivatized, marker-loaded liposomes, a test device produced by such a method, and methods of using the test device.

BACKGROUND OF THE INVENTION

Immunoassays, mainly in the form of enzyme-linked immunosorbent assays (ELISAs), have been widely used in the area of clinical diagnostic analysis (Gosling, *Clin. Chem.*, 36:1408-1427 (1990)). These methods offer high specificity, sensitivity, and ease of operation over other standard laboratory procedures. However, some of the disadvantages of the ELISA format which necessitate further improvement on the methodology include the lengthy time required for antigen-antibody reaction, reagent additions, enzymatic conversion of substrate, and several washing steps between the various operations.

As an alternative to the use of enzymes, liposomes are of interest as detectable labels in immunoassays because of their potential for immediate signal amplification. Liposomes are spherical vesicles in which an aqueous volume is enclosed by a bilayer membrane composed of phospholipid molecules (New, *Liposomes: A Practical Approach*, IRL Press, Oxford (1990)). Previous studies (Plant et al., *Anal. Biochem.*, 176: 420-426 (1989); Durst et al., In: GBF Monograph Series, Schmid, Ed., VCH, Weinheim, FRG, vol. 14, pp. 181-190 (1990) have demonstrated the advantages of liposome-encapsulated dye over enzymatically produced color in the enhancement of signals in competitive immunoassays. The capillary migration or lateral flow assay avoids separation and washing steps and long incubation times and yet attains sensitivity and specificity comparable to ELISAs. Nevertheless, the methodologies (Siebert et al., *Anal. Chim. Acta*, 282:297-305 (1993); Roberts et al., *Anal. Chem.*, 67:482-491 (1995); Siebert et al., *Anal. Chim. Acta*, 311 :309-318 (1995); Reeves et al., *Trends Anal. Chem.*, 14:351-355 (1995); Rule et al., *Clin. Chem.*, 42:1206-1209 (1996)) involve operations and solutions that make the handling of the sample and reagents susceptible to errors and more difficult to use for untrained personnel.

The driving force behind the formation of liposomes is hydration, so that when water is removed from lipid membranes, a shift in the phase transition occurs and a phase separation of lipids can take place resulting in aggregation and fusion of the liposomes, thereby losing the barrier function of the membrane (Lasiv, *Biochim. Biophys. Acta*, 692: 501-502 (1982); Mobley et al., *J. Control Release*, 31:73-87 (1994); Crowe et al., *cryobiology*, 19:317-328 (1982); Lin et al., *Stud. Biophys.*, 127:.99-104 (1988); Crowe et al., *J. Bioenerg. Biomembr.*, 21:77-92 (1989)).

The present invention is directed to overcoming the above-noted deficiencies in the prior art.

SUMMARY OF THE INVENTION

The present invention relates to a method for making a test device for detecting or quantifying an analyte in a sample. This method involves contacting a membrane with a mixture including derivatized, marker-loaded liposomes, and substantially dehydrating the mixture on the membrane under vacuum pressure at a temperature of from about 4° C. to about 80° C., wherein said mixture further includes one or more sugars in an amount sufficient to promote the stability of the liposomes during dehydration and rehydration.

The present invention also relates to a test device and its use in a method for detecting or quantifying an analyte in a sample. The test device includes a membrane which includes an immobilized liposome zone, wherein the immobilized liposome zone has bound thereto dehydrated, derivatized, marker-loaded liposomes dehydrated under vacuum pressure at a temperature of from about 4° C. to about 80° C. from a mixture which includes one or more sugars in an amount sufficient to promote the stability of the liposomes during dehydration and rehydration. The test device preferably includes a capture zone having a first binding material specific for the analyte bound thereto.

The method for detecting or quantifying an analyte in a test sample includes providing a test device in accordance with the present invention, wherein the dehydrated, derivatized, marker-loaded liposomes are derivatized with an analyte analog, contacting the test device with a solution of the sample, allowing the solution to migrate through the immobilized liposome zone and into the capture zone by capillary action, wherein the solution rehydrates the dehydrated, derivatized, marker-loaded liposomes which migrate with the solution into the capture zone by capillary action, permitting any competition to occur between any analyte present in the sample and the rehydrated derivatized, marker-loaded liposomes for the first binding material, after said permitting, detecting or quantifying the derivatized, marker-loaded liposomes in the capture zone, and correlating the presence or amount of the derivatized, marker-loaded liposomes in the capture zone with the presence or amount of the analyte in the sample.

The method of detecting or quantifying an analyte in a sample also includes providing a test device in accordance with the present invention, wherein the dehydrated, derivatized, marker-loaded liposomes are derivatized with a second binding material specific for the analyte and wherein the first binding material binds with a portion of the analyte other than a portion of the analyte for which the second binding material is selected, contacting the test device with a solution of said sample, allowing the solution to migrate through the immobilized liposome zone and into the capture zone by capillary action, wherein the solution rehydrates the dehydrated, derivatized, marker-loaded liposomes which migrate with the solution into the capture zone by capillary action, detecting or quantifying the derivatized, marker-loaded liposomes in the capture zone, and correlating the presence or amount of the derivatized, marker-loaded liposomes in the capture zone with the presence or amount of the analyte in the sample.

In the method of making the test device of the present invention, simple dehydration in a vacuum oven allows the liposomes to rehydrate more quickly because the liposomes remain partially hydrated. In addition, simple dehydration is less expensive, faster, and produces more stable liposomes than freeze-drying procedures.

Moreover, the device can be used directly in the field. The device is used only once, and, therefore, is free from residual environmental contaminants other than what may be present in the sample to be measured. Samples can be assayed within minutes after collection, with the results immediately available on-site. In addition, the device and method of the invention are less complex than many of the prior materials and methods. For example, a visible dye can be used as the detectable marker, eliminating the need for any detection or measurement instrumentation, and a separate marker or indicator step is not required with any embodiment of the invention.

DETAILED DESCRIPTION OF THE INVENTION

Figure 1:
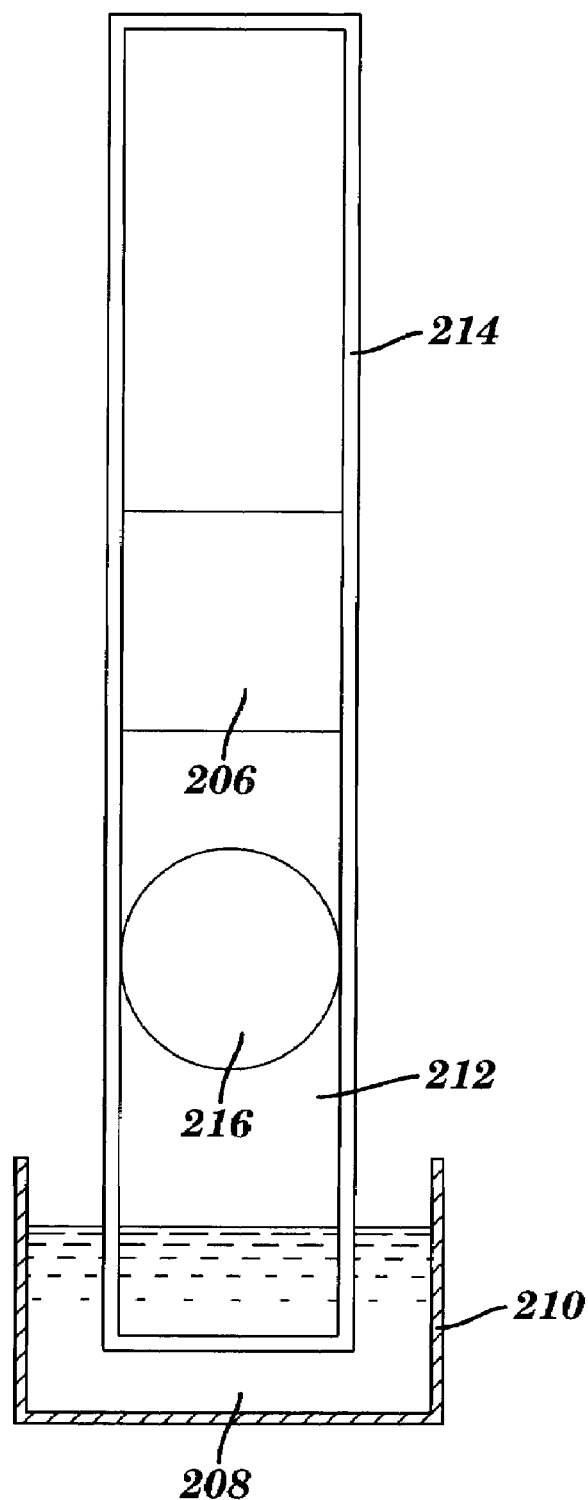
FIG. 1 is a schematic of a test device of the present invention.

As described above, the present invention relates to a method for making a test device for detecting or quantifying an analyte in a sample. This method involves contacting a membrane with a mixture including derivatized, marker-loaded liposomes, and substantially dehydrating the mixture on the membrane under vacuum pressure at a temperature of from about 4° C. to about 80° C., wherein said mixture further includes one or more sugars in an amount sufficient to promote the stability of the liposomes during dehydration and rehydration.

The present invention also relates to a test device for detecting or quantifying an analyte in a sample including a membrane which includes an immobilized liposome zone, wherein the immobilized liposome zone has bound thereto dehydrated, derivatized, marker-loaded liposomes dehydrated under vacuum pressure at a temperature of from about 4° C. to about 80° C. from a mixture which includes one or more sugars in an amount sufficient to promote the stability of the liposomes during dehydration and rehydration. Preferably, the test device also includes a capture zone having a first binding material specific for the analyte bound thereto.

The invention further provides a method for detecting or quantifying an analyte in a test sample by providing a test device in accordance with the present invention, wherein the dehydrated, derivatized, marker-loaded liposomes are derivatized with an analyte analog, contacting the test device with a solution of the sample, allowing the solution to migrate through the immobilized liposome zone and into the capture zone by capillary action, wherein the solution rehydrates the dehydrated, derivatized, marker-loaded liposomes which migrate with the solution into the capture zone by capillary action, permitting any competition to occur between any analyte present in the sample and the rehydrated derivatized, marker-loaded liposomes for the first binding material, after said permitting, detecting or quantifying the derivatized, marker-loaded liposomes in the capture zone, and correlating the presence or amount of the derivatized, marker-loaded liposomes in the capture zone with the presence or amount of the analyte in the sample.

The method of detecting or quantifying an analyte in a sample also includes providing a test device in accordance with the present invention, wherein the dehydrated, derivatized, marker-loaded liposomes are derivatized with a second binding material specific for the analyte and wherein the first binding material binds with a portion of the analyte other than a portion of the analyte for which the second binding material is selected, contacting the test device with a solution of said sample, allowing the solution to migrate through the immobilized liposome zone and into the capture zone by capillary action. wherein the solution rehydrates the dehydrated, derivatized, marker-loaded liposomes which migrate with the solution into the capture zone by capillary action, detecting or quantifying the derivatized, marker-loaded liposomes in the capture zone, and correlating the presence or amount of the derivatized, marker-loaded liposomes in the capture zone with the presence or amount of the analyte in the sample.

By "analyte" is meant the compound or composition to be measured or detected. A preferred analyte is a nucleic acid molecule.

By "mixture" is meant a solution, suspension, dispersion, or other mixture.

In one embodiment, the method of making the test device of the present invention further includes immobilizing a first binding material specific for the analyte in a capture zone on the membrane.

By "binding material" is meant a bioreceptor molecule such as an immunoglobulin or derivative or fragment thereof having an area on the surface or in a cavity which specifically binds to and is thereby defined as complementary with a particular spatial and polar organization of another molecule—in this case, the analyte. Alternatively, when the target analyte is a nucleic acid molecule, the first binding material is a nucleic acid molecule selected to hybridize with a portion of the target nucleic acid molecule.

Antibody binding materials can be monoclonal or polyclonal and can be prepared by techniques that are well known in the art such as immunization of a host and collection of sera or hybrid cell line technology. The binding material may also be any naturally occurring or synthetic compound that specifically binds the analyte of interest.

In one embodiment of the present invention, the derivatized, marker-loaded liposomes are derivatized with an analyte analog. This embodiment is particularly suitable for use of the test device in a competitive binding assay. Certain analytes of interest may be so intractable as to make direct conjugation with the liposome inconvenient, difficult, or even impossible. In such cases, it will be necessary to employ a reactive analog of the analyte of interest to prepare the derivatized liposomes. Thus, by "analyte analog" is meant the analyte or an analog of which will react with or bind to the liposomes. When an analog is employed, however, it is necessary that the particular characteristics of the analyte necessary for recognition by the first binding material in the competition reaction be present in the analyte analog conjugated with the liposomes.

In another embodiment, the derivatized, marker-loaded liposomes are derivatized with a second binding material. This embodiment is particularly suitable for use of the test device in a "sandwich" assay. The second binding material may be conjugated to the liposome surface. The second binding material must be bound to the liposomes so as to present a portion of the second binding material that may be recognized by the analyte.

Suitable conjugation methods are discussed in U.S. Pat. Nos. 5,789,154, 5,756,362, and 5,753,519, which are hereby incorporated by reference. For example, the liposome surface may be activated with thiol groups and coupled to a maleimide group on the second binding material. Or, conversely, maleimide-activated liposomes and thiol group-activated second binding material may be employed.

When present, the first and second binding materials are selected to bind specifically to separate portions of the analyte. For example, when the analyte is a nucleic acid sequence, it is necessary to choose probes for separate portions of the target nucleic acid sequence. Techniques for designing such probes are well-known. Probes suitable for the practice of the present invention must be complementary to the target analyte sequence, i.e., capable of hybridizing to the target, and should be highly specific for the target analyte. The probes are preferably between 17 and 25 nucleotides long, to provide the requisite specificity while avoiding unduly long hybridization times and minimizing the potential for formation of secondary structures under the assay conditions. In addition, the first and second binding materials (capture and reporter probes) should not be capable of hybridizing with one another. Techniques for identifying probes suitable for the practice of the invention are described in Sambrook et al., *Molecular Cloning: A Laboratory Manual*, Cold Spring Harbor Laboratory Press (1989), which is hereby incorporated by reference. A software program known as "Lasergene", available from DNASTAR, may optionally be used.

In general, to design an assay, the target nucleic acid is extracted from a sample, and then amplified by one of a variety of known amplification techniques. Such amplification techniques include polymerase chain reaction, ligase chain reaction, and Nucleic Acid Sequence Based Amplification (NASBA). See Kievits et al., "NASBA isothermal enzymatic in vitro nucleic acid amplification optimized for the diagnosis of HIV-1 infection" *J. of Virological Methods*, 35:273-286 (1991), which is hereby incorporated by reference. NASBA, marketed by Organon-Teknika, is a preferred amplification technique when information regarding the presence or concentration of viable organisms in a sample.

As hereinabove indicated, the methods and test device of the present invention include a marker within the interior of the liposomes. Suitable markers include fluorescent dyes, visible dyes, bio- and chemiluminescent materials, enzymatic substrates, radioactive materials, and electrochemical markers. Visible dyes and radioactive materials can be measured without lysis of the liposomes. Lysis of the liposomes in the capture zone may be accomplished by applying a liposome lysing agent to the capture zone. Suitable liposome lysing materials include surfactants such as octylglucopyranoside, sodium dioxycholate, sodium dodecylsulfate, polyoxyethylenesorbitan monolaurate sold by Sigma under the trademark Tween-20, and a non-ionic surfactant sold by Sigma under the trademark Triton X-100, which is t-octylphenoxypolyethoxyethanol. Octylglucopyranoside is a preferred lysing agent for many assays, because it lyses liposomes rapidly and does not appear to interfere with signal measurement. Alternatively, complement lysis of liposomes may be employed, or the liposomes can be ruptured with electrical, optical, thermal, or other physical means.

A qualitative or semi-quantitative measurement of the presence or amount of an analyte of interest may be made with the unaided eye when visible dyes are used as the marker. Alternatively, when greater precision is desired, or when the marker used necessitates instrumental analysis, the intensity of the marker may be measured directly on the membrane using a quantitative instrument such as a reflectometer, fluorimeter, spectrophotometer, etc.

In one embodiment of the invention, a marker which is visible under the assay conditions is used so that the presence and/or amount of analyte may be determined without further treatment and without the use of instrumentation, e.g., by use of liposomes containing a dye as the marker.

Alternatively, the methods and test device of the present invention may be modified to use an electrochemical marker. Suitable electrochemical markers, as well as methods for selecting them and using them are disclosed in U.S. Pat. No. 5,958,791 to Roberts et al. and co-pending U.S. patent application Ser. No. 09/315,576, filed May 20, 1999, which are hereby incorporated by reference. In particular, U.S. Pat. No. 5,958,791 to Roberts et al, teaches the formation of substrate-backed electrodes for use with electrochemical markers (see, e.g., col. 23, lines 56-64). Such substrate-backed electrodes include silicon-, borosilicate glass-, and quartz-backed electrodes.

In a preferred embodiment of the present invention, the membrane is an absorbent material.

By "absorbent material" is meant a porous material having a pore size of from 0.05 μm to 50 μm, preferably from 0.45 μm to 5 μm, which is susceptible to traversal by an aqueous medium in response to capillary force. Such materials may be natural polymeric materials, particularly cellulosic materials, such as fiber-containing papers, e.g., filter paper, chromatographic paper, etc.; synthetic or modified naturally occurring polymers, such as nitrocellulose, cellulose acetate, poly(vinyl chloride), polyacrylamide, cross linked dextran, agarose, polyacrylate, nylon, activated nylon, polysulfone base modified, etc.; glass fiber, such as borosilicate glass fiber and glass fiber with polyvinyl alcohol binder (available from Ahlstrom); woven fabric; nonwoven fabric; nonwoven veils; nonwoven materials; polyester fabrics and polyester blend fabrics (available from DuPont, Sontara Technologies); spunbonded polyester (available from Ahlstrom and DuPont); polypropylene screening fabrics (available from Sefar); rayon; cellulose/rayon; mixed cellulose and glass fiber; polyethersulfone (available from Pall Gelman Sciences); either used by themselves or in conjunction with a support, as described below.

Preferred absorbent materials include nitrocellulose, glass fiber, woven fabric, nylon, nonwoven material, polyester fabric, rayon, cellulose rayon blend, mixed fibers of cellulose and glass, or polyethersulfone.

It is to be understood that the term "nitrocellulose" refers to nitric acid esters of cellulose, which may be nitrocellulose alone, or a mixed ester of nitric acid and other acids, and in particular, aliphatic carboxylic acids having from one to seven carbon atoms, with acetic acid being preferred. Such materials, which are formed from cellulose esterified with nitric acid alone, or a mixture of nitric acid and another acid such as acetic acid, are often referred to as nitrocellulose paper.

The absorbent materials may be polyfunctional or be capable of being polyfunctionalized to permit immobilization of the second binding material.

Materials having a surface area sufficient for supporting the binding material and any other agents to be immobilized thereon as described herein may be employed for producing test devices in accordance with the present invention.

The test device of the present invention may include one or more absorbent materials (i.e., membranes), as described in co-pending U.S. patent application Ser. No. 09/315,576, filed May 20, 1999, which is hereby incorporated by reference. Regardless of the number of absorbent pads or materials employed, it is important that at least that portion of the test strip comprising and between the immobilized liposome zone and capture zone be made of a non-liposome lysing material. The material on which the first binding material is immobilized must be capable of supporting the immobilization, and the material(s) must allow liquid migration (lateral flow).

Absorbent materials having high surface areas (such as nitrocellulose) are particularly preferred for some applications in that the first binding material and the derivatized, marker-loaded liposomes, may be supported on such materials in high concentrations. It is to be understood, however, that the concentration of binding material which is actually used is dependent in part on the binding affinity of the first binding material. Accordingly, the scope of the invention is not limited to a particular concentration of first binding material on the absorbent material.

Application of the first binding material to the membrane may be accomplished by well-known techniques, for example, by spraying or spotting solutions of this component onto the membrane.

The first binding material can be bound to the membrane by covalent bonding. For example, the material to be bound can be applied directly to the membrane, and then bonded thereto via ultraviolet radiation. Alternatively, materials can be adsorbed onto the membrane, as long as the binding of the first binding material to the membrane is non-diffusive. This will involve contacting the membrane with a solution containing the material to be bound to the membrane and allowing the membrane to dry. In general, this procedure will be useful only where the membrane is relatively hydrophobic or has a high surface charge, and subsequent treatment with proteins, detergents, polysaccharides, or other materials capable of blocking nonspecific binding sites will be required.

The first binding material is preferably indirectly bound to the membrane in the capture zone of the device. For example, the first binding material is preferably labeled with a tag, for example, biotin, and a ligand that specifically binds the tag, for example, streptavidin or anti-biotin antibody, is premixed with the first binding material labeled with the tag and then applied to the membrane in the capture zone. Other agents suitable for immobilizing the first binding material in the capture zone include any compounds or antibodies that specifically bind a chosen tag used as a label for the first binding material, e.g., avidin, anti-fluorescein, anti-digoxin, and anti-dinitrophenyl (DNP).

Before or after application of the first binding material to the appropriate portion on the membrane, the residual non-specific binding capacity of the membrane can be, and preferably is, saturated or blocked with blocking agents which typically include a combination of three compounds: proteins, synthetic polymers, and surfactants, and which do not specifically bind the materials to be employed in the assay. Blocking is generally carried out after the first binding material is applied to the membrane, but it may be possible to block the membrane before this component is applied depending on the method of application, the particular blocking agent, and membrane employed. Thus, for example, the residual binding capacity of the substrate may be blocked so as to prevent nonspecific binding by the use of bovine serum albumin, as described in Towbin et al., *Proc. Nat'l. Acad. Sci.*, 76:4350 (1979), which is hereby incorporated by reference. The techniques for preventing non-specific binding are generally known in the art, and such techniques are also generally applicable to preventing nonspecific binding in the assay of the present invention. Examples of particularly suitable techniques for blocking with polyvinylpyrrolidone and polyvinylalcohol are described, for example, Bartles et al., *Anal. Biochem.*, 140:784 (1984), and in British Patent Specification GB 2204398 A, respectively, which are hereby incorporated by reference. Alternatively, one or more blocking agents can be incorporated into the buffer solution used to wash or carry test components along the membrane(s).

The blocking agents block nonspecific binding sites on the membrane. Thus, preferred blocking agents preferentially bind to the membrane. The blocking agents are selected from the group consisting of proteinaceous blocking reagents capable of inhibiting binding of molecules having a molecular weight of greater than about 1000 with said membrane and polymer blocking reagents capable of inhibiting binding of molecules having a molecular weight of less than about 1000 with said membrane. The proteinaceous blocking reagent may be selected from the group consisting of gelatin, non-fat dry milk, bovine serum albumin, albumins from other sources, keyhold limpet hemocyanin, casein, gum arabic, fish gelatin, ovalbumin, and horse serum. The polymer blocking reagent may be selected from the group consisting of polyvinylpyrrolidone, polyvinyl alcohol, and hydroxypropylmethyl cellulose. The blocking reagent is preferably a mixture of the above-identified blocking reagents.

Preferably, the blocking agents include a combination of polyvinylpyrrolidone and one or a mixture of proteins, such as gelatin, non-fat dry milk, bovine serum albumin, and casein. For liposomes derivatized with small analyte analogs, preferred concentrations of blocking agents dissolved in, e.g., Tris(hydroxymethyl)aminomethane-buffered saline, include from about 0.01 w/v % to about 1 w/v % polyvinylpyrrolidone and one or a mixture of: from about 0.01 w/v % to about 1 w/v % gelatin, from about 0.01 w/v % to about 1 w/v % non-fat dry milk, and from about 0.01 w/v % to about 0.05 w/v % bovine serum albumin. For liposomes derivatized with larger analyte analogs, e.g., antibodies and nucleotides, preferred concentrations of blocking agents dissolved in, e.g., Tris(hydroxymethyl)aminomethane-buffered saline, include from about 0.001 w/v % to about 2 w/v % polyvinylpyrrolidone and one or a mixture of: from about 0.02 w/v % to about 1 w/v % gelatin, from about 0.02 w/v % to about 1 w/v% non-fat dry milk, from about 0.02 w/v % to about 1 w/v % bovine serum albumin, and from about 0.01 w/v % to about 0.3 w/v % casein.

In conjunction with a blocking reagent or reagents, a surfactant may be applied to the membrane in a concentration sufficient to promote homogeneous flow of the test solution across the test device, to facilitate migration of the derivatized, marker-loaded liposomes without lysis of the liposomes. Suitable surfactants include Brij™ (polyoxyethylene ether), Tween 20™ (polyoxyethylenesorbitan monolaurate), Triton X 100™ (t-octylphenoxypolyethoxyethanol), sodium dodecylsulfate, n-octyl- -D-glucopyranoside, Span 20™, Nonindet P-40, Chapso™, Turgitol™ and sodium dioxycholate. The concentration of the surfactant(s) employed in a blocking solution will depend, in part, upon the liposome composition. In general, surfactants may be incorporated in a concentration of from about 0 to about 0.01 volume percent of the blocking solution, preferably from about 0.001 to about 0.005 volume percent of the blocking solution. It is important that the concentration of surfactant applied to the absorbent material be controlled, as premature lysis of the liposomes may occur if the surfactant concentration is too high. Preferred surfactants include polyoxyethylene ethers, polyoxyethylenesorbitan monolaurate, t-octylphenoxypolyethoxyethanol, sodium dodecylsulfate, octylglucopyranoside, and sodium dioxycholate.

Blocking agents are applied in a buffer solution to the membrane. Suitable buffers solutions include Tris(hydroxymethyl)aminomethane/HCl (Tris/HCl), Tris/citrate, Tris/maleate, Tris/glycine, phosphate buffer, HEPES, and other biological buffers in the correct pH range.

The membrane can be a single structure such as a sheet cut into strips. The membrane can be mounted on a support material, described more fully below. On the other hand, the membrane may provide its own support. In one embodiment of the invention, the test device includes a strip of particulate material bound to a support or solid surface such as found, for example, in thin-layer chromatography. The membrane can be a sheet having lanes thereon, or be a uniform sheet capable of division into separate lanes by physical removal of the absorbent material from the support to induce lane formation, wherein a separate assay can be performed in each lane as shown U.S. Pat. No. 5,958,791 to Roberts et al., which is hereby incorporated by reference. The membranes can be of a variety of shapes, including rectangular, circular, oval, trigonal, or the like, provided that there is at least one direction of traversal of a test mixture by capillary migration. Other directions of traversal may occur such as in an oval or circular piece contacted in the center with the test mixture. However, the main consideration is that there be one direction of flow from the immobilized liposome zone through the capture zone. In this discussion, strips of membrane support are described by way of illustration and not limitation.

The derivatized, marker-loaded liposomes are introduced onto the test device by simple dehydration under vacuum pressure. In particular, a mixture comprising derivatized, marker-loaded liposomes and one or more sugars in an amount sufficient to promote the stability of the liposomes during dehydration and rehydration is applied to an appropriate portion of the membrane. The membrane is then dried in a vacuum oven at temperatures as high as the membrane and liposomes can resist, typically at from about 4° C. to about 80° C., more preferably from about 4° C. to about 50° C., and, most preferably from about 10° C. to about 50° C., adjusting the drying time accordingly.

As described above, the method of making the test device of the present invention includes providing a mixture including derivatized, marker-loaded liposomes and one or more sugars in an amount sufficient to promote the stability of the liposomes during dehydration and rehydration. Suitable sugars include, but are not limited to, sucrose, trehalose, maltose, glucose, lactose, and mixtures thereof.

Preferably, the mixture includes from about 0.1M to about 2M sugars, more preferably, from about 0.7M to about 1M.

In one embodiment, the derivatized, marker-loaded liposomes also include one or more sugars entrapped within the liposomes, i.e., sugar present both inside and outside the vesicles. Suitable sugars are described above. Methods for providing liposomes with entrapped sugars and known in the art and are described in, for example, Example II of the present application, Madden et al., *Biochimica et Biophysica Acta*, 817:67-74 (1985), and Harrigan et al., *Chemistry and Physics of Lipids*, 52:139-149 (1990), which are hereby incorporated by reference.

In a preferred embodiment, the one or more sugars are present solely in the mixture, i.e., solely on the outside of the vesicles.

As described above, the method of making a test device according to the present invention includes substantially dehydrating the mixture including derivatized, marker-loaded liposomes on the membrane under vacuum pressure. Suitable vacuum pressures include from about 5 to about 25 psi, more preferably, from about 10 to about 15 psi, with dehydration time varying with vacuum pressure.

The migration of the test sample is preferably assisted by introducing a wicking reagent, preferably a buffer solution, onto the membrane to carry the test components along the support. Alternatively, if the sample volume is sufficiently large, it is not necessary to employ a separate buffer solution.

The support for the membrane where a support is desired or necessary will normally be hydrophobic, water insoluble, non-porous, and rigid, and usually will be of the same length and width as the absorbent strip but may be larger or smaller. A wide variety of organic and inorganic materials, both natural and synthetic, and combinations thereof, may be employed, provided only that the support does not interfere with the production of signal from the marker. Illustrative polymers include polyethylene, polypropylene, poly(4-methylbutene), polystyrene, polymethacrylate, poly(ethylene terephthalate), nylon, poly(vinyl chloride) poly(vinyl butyrate), glass, ceramics, metals, and the like.

The sizes of the pieces of membrane are dependent on several considerations. The following discussion is primarily focused on strips of membrane for purpose of illustration and not limitation. As mentioned above, other shapes such as circular, oval, trigonal, and the like, fall equally within the scope of this invention. The dimensions thereof and other parameters can be determined by those skilled in the art with reference to the disclosure herein.

When capillary flow is predominantly upward, the pore size length, and thickness of the strip control the amount of mixture that can pass through the capture zone. If the transfer of a large volume of test mixture is desired, the fluid capacity of the strip beyond the capture zone must be sufficient to accommodate the desired volume. Alternatively, an additional absorbent material, absorbing pad, or sponge, referred to herein as a wicking pad, may be used to contact the end of the membrane beyond the capture zone. A wicking pad may be used in this manner in situations when it is desirable to pull a larger volume of the test mixture across the test device.

To permit conservation of reagents and provide for samples of limited size, the width of the strip will generally be relatively narrow, usually less than 20 mm preferably less than 10 mm. Generally, the width of the strip will not be less than about 2 mm and will usually range from about 2 mm to 10 mm, preferably from about 3 mm to 6 mm.

As is described in detail below, the test device in accordance with the invention may be modified for simultaneous multiple analyte detection or determination. The length of the strip will depend on the concentration of the analyte and practical considerations such as ease of handling and the number of measurement portions on the strip and will be about 4 cm to 20 cm, usually about 5 cm to 15 cm, preferably about 6 to 13 cm but may be of any practical length. The structure of the strip can be varied widely and includes fine, medium fine, medium, medium coarse, and coarse. Selection of the porosity of the material may be based on the rate of binding of the components for a given assay.

In one preferred embodiment, a test device according to the present invention is made by coating a first binding material onto the membrane at an appropriate portion and then drying the membrane, preferably, under vacuum pressure. Subsequently, the membrane is blocked and dried, preferably under vacuum pressure, for a suitable time determined by the membrane and blocking agents used. The derivatized, marker-loaded liposomes are then applied at an appropriate portion on the membrane and the membrane is again dried under vacuum pressure.

FIG. 1 shows a test device in accordance with the present invention, depicted immediately after insertion into test sample 208, which is held in tray 210. As shown in FIG. 1, membrane 212 is mounted on a support 214. The test device shown in FIG. 1 includes an immobilized liposome zone 216 which, as described above, has dehydrated, derivatized, marker-loaded liposomes bound thereto and a capture zone 206, which, as described above, has a first binding material for the appropriate derivatized, marker-loaded liposomes bound thereto.

In use in a competition format of the present invention, the membrane 212 is inserted into the test sample 208. Wetting of the membrane 212 by capillary action is allowed to continue at least until capture zone 206 is wet (and preferably, until the solvent front reaches the end of the membrane) with test sample 208, respectively. Test sample 208 traverses the test device into and through immobilized liposome zone 216, where dehydrated, analyte analog-tagged, marker-loaded liposomes are rehydrated. The test sample 208 continues to traverse the test device into and through capture zone 206, where competition occurs between the rehydrated, analyte-analog tagged, marker-loaded liposomes and the analyte in the test sample for binding sites with the first binding material bound in the capture zone 206. More liposomes will bind to the capture zone when there is less analyte in the sample, thus, the intensity of the marker in the capture zone varies inversely with the concentration of analyte in the test sample.

The test sample may be derived from a wide variety of sources, such as physiologic fluids, illustrated by saliva, sweat, serum, plasma, urine, tear fluid, spinal fluid, etc., chemical processing streams, food, waste water, natural waters, soil extracts, etc. Various addenda may be added to adjust the properties of the test mixture, or of a carrier solution used as a wicking reagent, depending upon the properties of the other components of the device, as well as on those of the liposomes or the analyte analog-liposome conjugate, or the analyte itself. Examples of solution addenda which may be incorporated into test, control, or carrier solutions or mixtures in accordance with the invention include buffers, for example, pH and ionic strength, sample or analyte solubilizing agents, such as, for example, nonpolar solvents, and high molecular weight polymers such as Ficoll®, a nonionic synthetic polymer of sucrose, available from Pharmacia, and dextran.

In the method for detecting or quantifying an analyte in a sample of the present invention, the membrane is contacted with test mixture, for example, by immersing a contact portion of the absorbent material into the test mixture. Alternatively, the test mixture may be contacted with the membrane by spotting the test mixture onto the absorbent material in a contact portion, e.g., for lateral flow assays.

The movement of the test components along the membrane(s) is due to capillary action. This capillary movement along the membrane causes the test mixture to be carried to and through the capture zone, where measurement of the marker from the liposomes takes place.

In a preferred embodiment, the test device and methods of the present invention utilize lateral flow, rather than upward flow, to allow the test sample and rehydrated, derivatized, marker-loaded liposomes to migrate the test device.

If quantitative results are desired, wetting of the membrane and any other absorbent materials, if present, by capillary action is allowed to continue until a sufficient volume of test mixture and/or buffer solution has passed through the capture zone to ensure that any analyte present in the test mixture has reached the capture zone. If detection alone is desired, less care must be taken to ensure that all analyte has reached the capture zone. It is possible to "calibrate" run times and buffer volumes using pre-runs employing colorimetric detection as described herein and in Rule et al., *Clin. Chem.* 42:1206-1209 (1996), which is hereby incorporated by reference, or electrochemical detection as described in U.S. Pat. No. 5,958,791 and U.S. patent application Ser. No. 09/315,576, filed May 20, 1999, which are hereby incorporated by reference.

For the most part, relatively short times are involved for the test mixture to traverse the strip. Usually, traversal of the test mixture over the strip will take at least 30 seconds and not more than 45 minutes to 1 hour, more usually from about 1 minute to 10 minutes. In accordance with the method of the invention, the signal is rapidly, even immediately, detectable.

The conjugate of the second binding material or the analyte-analog and the marker-encapsulating liposomes may be prepared by procedures generally known in the art, with the particular procedure used in a given case being dependent upon the liposome components and binding material employed. Such techniques include covalent coupling, derivatization or activation, and the like. The liposomes may be produced from a component which has been derivatized with the second binding material or analyte analog, whereby the liposomes, when produced, are conjugated with the second binding material or analyte analog. In another procedure, the liposomes, including the marker, may be initially formed, followed by conjugating the liposomes with the second binding material or analyte analog by procedures known in the art.

Liposomes can be prepared from a wide variety of lipids, including phospholipids, glycolipids, steroids, relatively long chain alkyl esters; e.g., alkyl phosphates, fatty acid esters; e.g. lecithin, fatty amines, and the like. A mixture of fatty materials may be employed, such as a combination of neutral steroid, a charge amphiphile, and a phospholipid. Illustrative examples of phospholipids include lecithin, sphingomyelin, and dipalmitoylphosphatidylcholine, etc. Representative steroids include cholesterol, chlorestanol, lanosterol, and the like. Representative charge amphiphilic compounds generally contain from 12 to 30 carbon atoms. Mono- or dialkyl phosphate esters, or alkylamines; e.g. dicetyl phosphate, stearyl amine, hexadecyl amine, dilaurylphosphate, and the like are representative.

The liposome sacs are prepared in aqueous solution containing the marker whereby the sacs will include the marker in their interiors. The liposome sacs may be prepared by vigorous agitation in the solution, followed by removal of the unencapsulated marker. Further details with respect to the preparation of liposomes are set forth in U.S. Pat. No. 4,342, 826 and PCT International Publication No. WO 80/01515, both of which are incorporated by reference.

With the test device and method of the invention, one may also assay a test sample for a plurality of analytes such as toxic chemicals or pathogens, or screen for one or more of a plurality of analytes, as is known in the art.

As a matter of convenience, the present device can be provided in a kit in packaged combination with predetermined amounts of reagents for use in assaying for an analyte or a plurality of analytes. Aside from the test device with dehydrated, derivatized, marker-loaded liposomes, other additives such as ancillary reagents may be included, for example, stabilizers, buffers, and the like. The relative amounts of the various reagents may be varied widely, to provide for concentration in solution of the reagents which substantially optimize the sensitivity of the assay. The reagents can be provided as dry powders, usually lyophilized, including excipients. which on dissolution will provide for a reagent solution having the appropriate concentrations for performing the assay. The kit or package may include other components such as standards of the analyte or analytes (analyte samples having known concentrations of the analyte).

The present invention is applicable to procedures and products for determining a wide variety of analytes. As representative examples of types of analytes, there may be mentioned: environmental and food contaminants, including pesticides and toxic industrial chemicals; drugs, including therapeutic drugs and drugs of abuse; hormones, vitamins, proteins, including enzymes, receptors, and antibodies of all classes; prions; peptides; steroids; bacteria; fungi; viruses; parasites; components or products of bacteria, fungi, viruses, or parasites; aptamers; allergens of all types; products or components of normal or malignant cells; etc. As particular examples, there may be mentioned $T_4$; $T_3$; digoxin; hCG; insulin; theophylline; leutinizing hormones and organisms causing or associated with various disease states, such as *streptococcus* pyrogenes (group A), Herpes Simplex I and II, cytomegalovirus, chlamydiae, etc. The invention may also be used to determine relative antibody affinities, and for relative nucleic acid hybridization experiments. restriction enzyme assay with nucleic acids, and binding of proteins or other material to nucleic acids.

A device prepared in accordance with the present invention can be used in a variety of assays, such as competitive binding assays and sandwich assays. as described in U.S. Pat. No. 5,789,154 to Durst et al., U.S. Pat. No. 5,756,362 to Durst et al., U.S. Pat. No. 5,753,519 to Durst et al., U.S. Pat. No. 5,958,791 to Roberts et al., co-pending U.S. patent application Ser. No. 09/027,324, filed Feb. 20, 1998, co-pending U.S. patent application Ser. No. 09/034,086, filed Mar. 3, 1998, co-pending U.S. patent application Ser. No. 09/354,471, filed Jul. 15, 1999, and co-pending U.S. patent application Ser. No. 09/315,576, filed May 20, 1999, which are hereby incorporated by reference.

As hereinabove indicated, the assay may be qualitative (presence or absence of certain level of analyte) or quantitative or semi-quantitative. The preparation of suitable standards and/or standard curves is deemed to be within the scope of those skilled in the art from the teachings herein.

The methods of the invention, and preparation and use of the test device in accordance with the invention, are illustrated by the following Examples.

EXAMPLES

Example 1

Materials

Dipalmitoyl phosphatidyl choline (DPPC) and dipalmitoyl phosphatidyl glycerol (DPPG) were obtained from Avanti Polar Lipids, Inc. (Alabaster, Ala.). Sulforhodamine B (SRB), N-((6-(biotinoyl)amino)hexanoyl)-1,2-dihexadecanoyl-sn-glycero-3-phosphoethanolamine, triethylammonium salt (biotinylated DPPE), and D(+)-biotin were purchased from Molecular Probes (Eugene, Ore.). Polyvinylpyrrolidone (PVP, 10,000 Da), cholesterol, normal human serum (NHS), gelatin, bovine serum albumin (BSA), sucrose, trehalose, Tris(hydroxymethyl)aminomethane (Tris), Tween 20, and Sephadex G-50 were purchased from Sigma Chemical Co., (St. Louis, Mo.). Carnation brand nonfat dry milk (NFDM) was acquired locally. Polycarbonate syringe filters of 3-, 0.4-, and 0.2-μm pore sizes were purchased from Osmonics Laboratory Products (Livermore, Calif.) and Mylar-supported nitrocellulose membranes with 8-μm pore size were obtained from Sartorius Corp. (Goettingen, Germany) and Millipore Corp. (Bedford, Mass.). The detergent, n-octyl-β-D-glucopyranoside, was obtained from Pfanstiehl Laboratories, Inc. (Waukegan, Ill.).

Example 2

Preparation of Biotin-Tagged, Dye-Loaded Liposomes

Five batches of liposomes, labeled I to V, were prepared to study the stabilizing effect of sugar (trehalose) inside the liposomes. The batches were prepared by a modified reverse-phase evaporation method (Siebert et al., *Anal. Chim Acta*, 282:297-305 (1993); Szoka et al., *Biochim. Biophys. Acta*, 601:559-571 (1980); O'Connell et al., *Clin. Chem.*, 31:1424-1426 (1985, which are hereby incorporated by reference) from a mixture of DPPC, cholesterol, DPPG, and biotinylated DPPE in a molar ratio of 4.7:4.8:0.5:0.01. In the lumen of the liposomes was encapsulated the same concentration of sulforhodamine B (100 mM), increasing amounts of trehalose. and decreasing amounts of Tris/(hydroxymethyl)aminomethane/HCl (Tris/HCl) buffer, pH 7.0, to maintain an osmolality value of 827 mOsmol/kg for each preparation (see Table 1).

TABLE 1

Biotin-Tagged Liposome Characteristics

| | Liposome preparation | | | | | | | |
|---|---|---|---|---|---|---|---|---|
| | I | II | III | IV | V | VI | VII | VIII |
| Mean diameter* (nm) | 321 | 353 | 294 | 375 | 336 | 242 | 300 | 384 |
| Liposome concentration per ml | $5.5 \times 10^{12}$ | $3.6 \times 10^{12}$ | $7.9 \times 10^{12}$ | $6.3 \times 10^{12}$ | $3.1 \times 10^{12}$ | $3.1 \times 10^{12}$ | $1.5 \times 10^{12}$ | $8.3 \times 10^{11}$ |
| Trehalose concentration (mM) | 0 | 10 | 50 | 100 | 200 | 0 | 0 | 0 |
| SRB concentration (mM) | 100 | 100 | 100 | 100 | 100 | 175 | 175 | 175 |
| Biotin (molecules per liposome) | 719 | 870 | 603 | 982 | 788 | 409 | 628 | 1029 |
| Osmolality (mOsmol/kg) | 827 | 827 | 827 | 827 | 827 | 204 | 204 | 204 |

*Measured value.

Briefly, the procedure involved dissolving the lipids in a solvent mixture containing chloroform:isopropyl ether:methanol (6:6:1, v/v). The temperature was kept at 45° C. throughout the entire process. The encapsulant was added and the mixture was sonicated for 5 minutes under a low flow of nitrogen. The organic phase was removed under vacuum on a rotary evaporator. Another aliquot of encapsulant solution was added, and the liposome preparation was sonicated for an additional 30 minutes. The liposomes were then extruded sequentially three times through 3-, 0.4-, and 0.2-μm polycarbonate syringe filters arranged in tandem. To remove the unencapsulated dye, the preparation was gel filtered on a Sephadex G-50-150 column (Sigma Chemical Co., (St. Louis, Mo.)) equilibrated with the appropriate buffer which is similar in osmolality to the encapsulant solution and dialyzed against 1 liter of the same buffer.

Three other batches of liposomes, labeled VI to VIII, were prepared to study the effect of liposome size on stability. These batches were prepared by the same reverse-phase evaporation method using an encapsulant containing 175 mM sulforhodamine B in 0.02 M Tris/HCl, pH 7.5, buffer (osmolality of encapsulant equals 204 mOsmol/kg). The differences in the procedure for the three batches were in the length of sonication time to which each batch was subjected and the pore size of the filters used which resulted in differences in the liposome sizes. Longer sonication times produced smaller liposomes.

All liposomes were stored in buffers that were iso-osmolar or up to 100 mOsmol/kg above their respective encapsulant at 4° C. in the dark until needed.

Example 3

Characterization of the Liposomes

The mean diameter of the liposomes was measured by a laser-based light-scattering particle-size analyzer (PCS sizing system from Malvern Instruments Ltd, Malvern, UK). Fluorescence intensity measurements were carried out on a McPherson Model SF 750 spectrofluorometer (Acton, Mass.) operated at excitation and emission wave-lengths of 543 and 596 nm, respectively.

Example 4

Preparation of Antibiotin-Coated Test Strips

Antibiotin antibodies were immobilized on sheets of nitrocellulose membranes (45×160 mm) in a 2.5-mm-wide band, 15 mm from the bottom of the sheet using a microprocessor controlled Linomat IV TLC Sample Applicator (Camag Scientific, Inc., Wrightsville Beach, N.C.). The antibody-coated membranes were dried in a vacuum oven (15 psi) at room temperature for 1 hour and then immersed in various blocking agents dissolved in Tris-buffered saline (TBS; 0.02 M Tris/HCl, 0.15 M NaCl, and 0.01% $NaN_3$, pH 7.0) for 1 hour. The blocked membranes were dried at room temperature in a vacuum oven for different time periods and cut into strips (5×45 mm). Each test strip contained 4.5 μg of antibiotin in the capture zone. The strips were stored at 4° C. in vacuum-sealed plastic bags until ready for use.

Glazed strips were prepared by applying sucrose solutions of different concentrations, using the Linomat IV sample applicator, onto an area 6 mm below the antibiotin band on nitrocellulose membrane sheets previously coated with antibiotin antibodies and blocked with 0.2% PVP and 0.01% gelatin in TBS. The glazed membranes were air-dried for 1 hour before being cut into 5×45-mm strips and stored in vacuum-sealed plastic bags until ready for use.

Example 5

Dehydration of Liposomes on Antibiotin-Coated Strips

Liposome solutions were prepared using diluents containing different excipients in phosphate-buffered saline (PBS; 0.01 M $KH_2PO_4/K_2HPO_4$, 0.15 M NaCl, and 0.01% $NaN_3$, pH 7.0). One microliter of the diluted liposome solution was applied at a point 6 mm below the antibiotin band and immediately covered with aluminum foil to prevent lysis of sulforhodamine B (SRB)-loaded liposomes by light (SRB-encapsulated liposomes were observed to be slightly sensitive to light). The strips were dried in a vacuum oven (15 psi) at room temperature for 2 hours.

Strips without liposomes were also dried in the vacuum oven simultaneously with the test strips for use as controls. The purpose was to obtain the same degree of hydration in both the test strips and the controls.

For the experiments where the effects of sugar glaze under the dehydrated liposomes were investigated, 1 μL of the liposome solution was applied on top of the sugar glaze and also dried in the vacuum oven at room temperature for 2 hours.

Example 6

Recovery Test Protocol

The recovery test was performed by inserting the test strips into a test tube, or a holder device, containing PBS (pH 7.4) or NHS as carrier or mobile phase. When the solution front reached the top of the strip, the strip was removed and air-dried. The antibiotin capture zone collected the biotin-tagged liposomes that remained intact after the dehydration/rehydration process. The control consisted of applying 1 µL of the same liposome solution onto the control strips at a point 6 mm below the antibiotin band and, without drying, immediately inserting them into the test tubes containing the mobile phase.

Example 7

Biotin Assay Protocol

The assay was performed by inserting the test strips, which contained the dehydrated biotin-tagged, SRB-loaded liposomes at a zone below the antibiotin band, into test tubes holding the liquid sample or the calibration samples of biotin in PBS, TBS, or NHS. When the solution front reached the top of the strip, the strip was removed and air-dried.

Example 8

Detection and Quantitation

The color intensity of the antibiotin capture zone was measured optically. For a more accurate quantitation of the red coloration of the band, a Hewlett-Packard ScanJet IIc desktop scanner (Palo Alto, Calif.) and scan analysis densitometry software (Biosoft, Ferguson, Mo.) installed on a Macintosh Performa 636CD were used. This approach allowed the conversion of the red coloration into a gray-scale reading that could be quantified (Siebert et al., *Anal. Chim. Acta,* 282:297-305 (1993), which is hereby incorporated by reference). The results are represented in arbitrary units of the gray-scale intensity or as a percentage of recovery of the dehydrated/rehydrated liposomes when compared with the control, that is, assigning a value of 100% to the control.

Example 9

Liposome Characteristics

Sulforhodamine B fluorescence is self-quenching when encapsulated at high concentration, thus the integrity of the liposomes can be determined by measuring the fluorescence of a liposome solution before and after lysis of the liposomes. Total lysis of the liposomes was obtained by the addition of a solution of n-octyl β-D-glucopyranoside to a final concentration of 30 mM. The stability over time can be studied by measuring the percentage of free dye in the preparation. The measurement of dye encapsulated in the liposomes and the determination of liposomes size by the laser scattering method allowed the calculation of the liposome characteristics (see Table 1). All calculations were performed as previously described (Siebert et al., *Anal. Chim. Acta,* 282:297-305 (1993), which is hereby incorporated by reference), taking into account that the DPPE-biotin is 0.1 mol % of the total lipids and assuming that the dye encapsulated was equal in concentration to the original dye solution used, that the bilayer thickness is 4 nm, and that the average surface headgroup area of DPPC molecules and cholesterol molecules in a mixed bilayer is 0.71 and 0.19 $nm^2$, respectively (Israelachvili et al., *Biochim. Biophys. Acta,* 389:13-19 (1975), which is hereby incorporated by reference).

Example 10

Recovery of Dehydrated/Rehydrated Liposomes on Nitrocellulose Strips

Basically, two major points were important in the process of dehydration/rehydration of liposomes on nitrocellulose strips. The first was the determination of the appropriate blocking agents and drying conditions for the membranes, and the second was the study of the components of the liposome preparation, which included the encapsulant (internal), the excipient in the diluent (external), and the characteristics of the liposomes.

Initial testing involved the use of varying concentrations of different blocking agents prepared in Tris-buffered saline. Polyvinylpyrrolidone (PVP), gelatin, bovine serum albumin (BSA), and non-fat dry milk (NFDM) were tested at 0.02, 0.1, and 0.5%, and Tween 20 at 0.002 and 0.02%. Liposome batch VII (no internal trehalose) was diluted with phosphate buffered saline (PBS) (no excipients) and 1 µL was dehydrated on the blocked nitrocellulose strips below the antibiotin band as described above. Among the blocking agents tested, PVP provided the best protection of the liposomes after the dehydration/rehydration cycle, as indicated by the highest signal obtained at the antibiotin capture zone. Listed in order of decreasing effectiveness in preserving the dehydrated liposomes are the blocking agents at their individual optimal concentrations and the respective percentage of recovery of the liposomes obtained: 0.5% PVP (14.9% recovery)>0.1% gelatin (8.7% recovery)>0.02% BSA (3.7% recovery)>0.1% NFDM (2.5% recovery). The use of unblocked membranes (Tris-buffered saline-treated) and those blocked with Tween 20 resulted in complete lysis of the liposomes when the dried liposomes were rehydrated by the mobile phase.

Drying the blocked membrane overnight (14 hours) in the vacuum oven (15 psi) at room temperature resulted in very dry membranes. During the migration of the mobile phase, it was observed that the liquid took a long time (ca. 15 minutes) to migrate past the capture zone. In addition, the mobile phase migrated preferentially along the strip edges which reduced the chances of liposomes binding in the capture zone. By decreasing the drying time of the blocked membranes to 8 hours, the carrier solution migrated more rapidly and uniformly through the capture zone and the signal on the antibiotin band was improved.

Example 11

Effect of Sucrose Glaze on the Recovery of the Liposomes

Liposome batch I (no internal trehalose) was used to study the effect of sucrose glaze on the recovery of liposomes. The concentrations of sucrose tested ranged from zero to 4.4 µmol/strip. The results showed that the sucrose glaze, placed on the strips prior to the application of the liposome preparation for dehydration, provided a dramatic improvement in the recovery of the dehydrated/rehydrated liposomes. The glaze greatly diminished the aggregation observed previously at the point of application of the liposomes after the mobile phase passed by, and it considerably increased the intensity at the antibiotin band which indicated higher recovery of intact liposomes. The optimal amount of sucrose glaze was observed to be ca. 1.5 µmol/strip (see FIG. 2) and resulted in 70% recovery. At sucrose glazes greater than ca. 2.2 µmol/strip, the aggregation at the point of application of the liposomes completely disappeared, but the signal intensity at the antibiotin band decreased.

Example 12

Components of the Liposome Preparation

1. Sugar outside of the liposomes. Due to the observation that the sugar glaze greatly improved the preservation of the dehydrated/rehydrated liposomes, the effect of sugar added as excipient in the diluent for the liposome preparation prior to its application onto the strips was evaluated and compared with the results of the sugar glaze. Concentrations of sucrose and trehalose ranging from 0.07 to 0.6 M were prepared in PBS, pH 7.4, and used as diluent for liposome batch I (no internal trehalose). Without external sugar, aggregation appeared at the point of application of the liposomes after the mobile phase migrated past the dehydrated liposomes, and the antibiotin zone bound only very few liposomes, i.e., many of the liposomes lysed upon rehydration. As the concentration of sugars was increased, the aggregation at the point of application diminished until aggregation completely disappeared and concomitantly, the recovery of the dehydrated liposomes increased. Sucrose was observed to have a slightly better preservation effect than trehalose. An added advantage of choosing sucrose over trehalose is the lower cost. A study with higher concentrations of sucrose was carried out and the optimal concentration of external sucrose needed for stabilizing the dehydrated liposomes was observed to be in the range of 0.7 to 1.0 M or 0.7 to 1.0 µmol/µL/strip (see FIG. 2). At sucrose concentrations higher than 1.0 M, the recovery of the dehydrated liposomes decreased. In addition, the flow rate of the mobile phase with the high sucrose content became very slow after contacting the dehydrated liposomes. The uniformity of the capture zone also decreased. The slower flow rate can be explained by the increase in viscosity of the mobile phase due to the sucrose.

Figure 2:
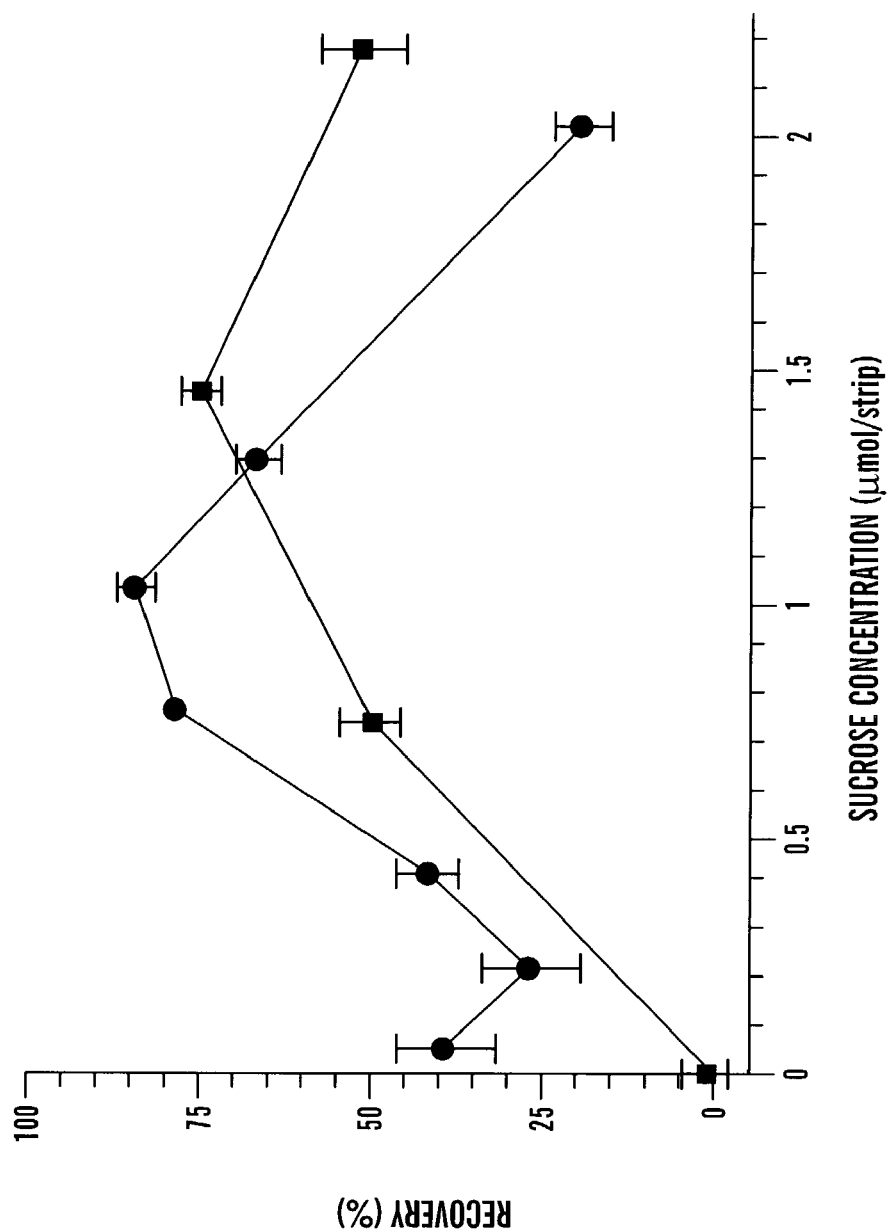
FIG. 2 is a graph showing the recovery of dehydrated liposomes on nitrocellulose strips with varying amounts of external sucrose in the form of a sucrose glaze (■) and as added excipient in the diluent (●). Nitrocellulose strips incorporating a 4.5 µg antibiotin band were used with phosphate buffered saline as the mobile phase. Each point is an average of at least three strips and one standard deviation is shown as an error bar.

The results shown in FIG. 2 indicated that less sucrose (0.7 to 1.0 µmol/µL/strip) was needed in the diluent for the liposomes compared to the sucrose glaze (1.5 µmol/strip) to achieve protection of the dehydrated liposomes. Moreover, with sucrose in the diluent, a higher degree of recovery was obtained. Considering these results and the ease of adding sucrose to the diluent versus application of the sugar glaze, the former method was chosen for the subsequent work.

2. Sugar inside of the liposomes. According to the literature (Crowe et al., Arch. Biochem. Biophys., 242:240-247 (1985); Madden et al., Biochim. Biophys. Acta, 817:67-74 (1985); Harrigan et al., Chem. Phys. Lipids, 52:139-149 (1990); Crowe et al., In: Liposome Technology, Gregoriandis, Ed., CRC Press, Boca Raton, Fla., vol. 1, pp. 229-270 (1993), which are hereby incorporated by reference). trehalose must be present both inside and outside of the vesicles to stabilize the liposomes during lyophilization and dehydration processes. For the purpose of finding the optimum internal concentration of trehalose, five batches of liposomes were prepared entrapping the following concentrations of trehalose: 0, 10, 50, 100. and 200 mM (see Table 1). The different batches of liposomes were diluted with PBS containing 0.42 M sucrose before application onto the nitrocellulose strips for dehydration. The results shown in FIG. 3 indicated that, in the presence of sucrose outside the liposomes, trehalose encapsulated in the liposomes did not improve the stability of the liposomes undergoing the dehydration/rehydration process on nitrocellulose membranes. Internal trehalose concentrations higher than 100 mM may even have a destabilizing effect on the liposomes. These liposome stability results obtained on nitrocellulose membranes are in contrast to the positive effect of both internal and external trehalose reported for lyophilized liposomes (Crowe et al., Arch. Biochem. Biophys., 242:240-247 (1985); Madden et al., Biochim. Biophys. Acta, 817:67-74 (1985); Crowe et al., In: Liposome Technology, Gregoriandis, Ed., CRC Press, Boca Raton, Fla., vol. 1, pp. 229-270 (1993), which are hereby incorporated by reference) and dehydrated liposomes (Harrigan et al., Chem. Phys. Lipids, 52:139-149 (1990), which is hereby incorporated by reference). One possible explanation might be differences in the lipid composition of the liposomes used in this study versus the ones reported. Another might be the different physical characteristics of these liposomes when dehydrated on membranes compared to those in the frozen or dehydrated state.

Example 13

Effect of Liposome Size on Stability

Figure 4:
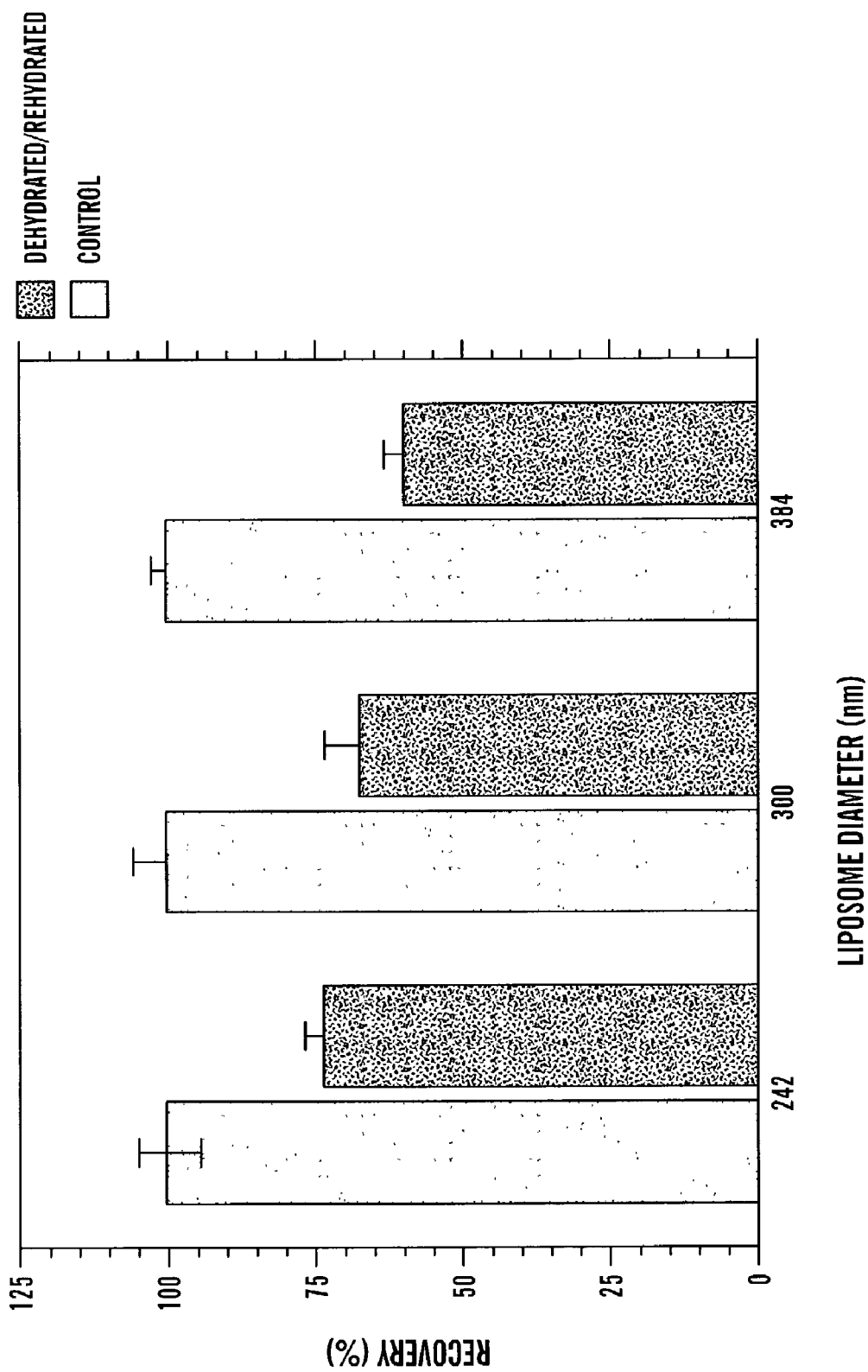
FIG. 4 is a graph showing the recovery after the dehydration/rehydration process for liposomes of varying sizes. Nitrocellulose strips incorporating a 4.5 µg antibiotin band were used with approximately $5.3 \times 10^8$ biotin-tagged liposomes and normal human serum as the mobile phase. Each point is an average of four strips and one standard deviation is shown as an error bar.

Three preparations of liposomes which were 242, 300, and 384 nm in diameter (batches VI, VII, and VIII in Table 1) were studied. Although several reports (Harrigan et al., Chem. Phys. Lipids, 52:139-149 (1990); Crowe et al., In: Liposome Technology, Gregoriandis, Ed., CRC Press, Boca Raton, Fla., vol. 1, pp. 229-270 (1993); Crowe et al., Biochim. Biophys. Acta, 939:327-334 (1988), which are hereby incorporated by reference) showed that vesicles larger than 200 nm in diameter were less stable than smaller ones, the stability of the larger liposomes was investigated because of the previous observation that greater signal intensities could be obtained with larger liposomes. While the results in FIG. 4 show that there is a slight increase in the recovery for the smaller liposomes, liposomes with diameters ranging from 242 to 384 nm may be recovered successfully after a dehydration/rehydration process, making them useful in a one-step strip assay.

Example 14

Effect of Number of Liposomes

Figure 5:
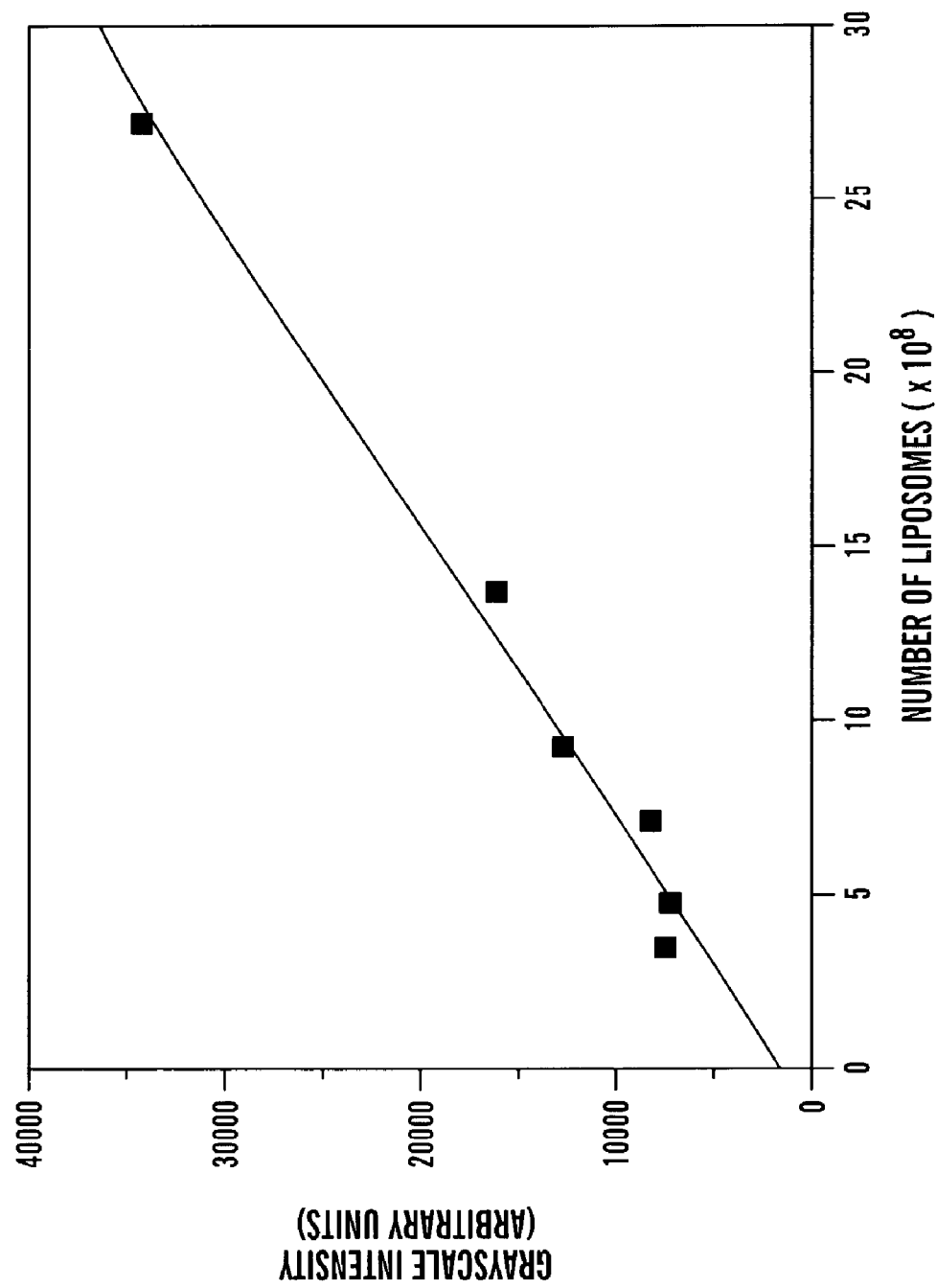
FIG. 5 is a graph showing the relationship between number of liposomes dehydrated on the nitrocellulose strips and grayscale intensity of the antibody zone. Nitrocellulose strips incorporating a 4.5 µg antibiotin band were used with normal human serum as the mobile phase.

The results of FIG. 5 show a positive linear correlation between gray-scale intensity of the binding zone and the number of liposomes dehydrated on the nitrocellulose strip. However, the percentage of liposomes recovered upon rehydration remained constant. That is, liposomes within the range needed to produce a distinguishable signal ($2.5 \times 10^8$ to $2 \times 10^9$ liposomes/strip) provided the same percentage of recovery (75%) after the dehydration/rehydration process. Although a higher signal was obtained as the number of dehydrated liposomes increased, greater amounts of analyte were needed to compete with the analyte tags on the liposomes. Thus, to keep the limit of detection low, one must select an amount of liposomes that will give a strong enough signal for the zero standard and yet be able to provide a signal for the lowest possible concentration of analyte that is distinguishable from the zero standard. The number of liposomes that provided the best response curve was between $7 \times 10^8$ and $9 \times 10^8$ liposomes per strip containing 4.5 µg of antibiotin at the binding zone.

Example 15

Effect of Osmolality Inside of the Liposomes

Figure 3:
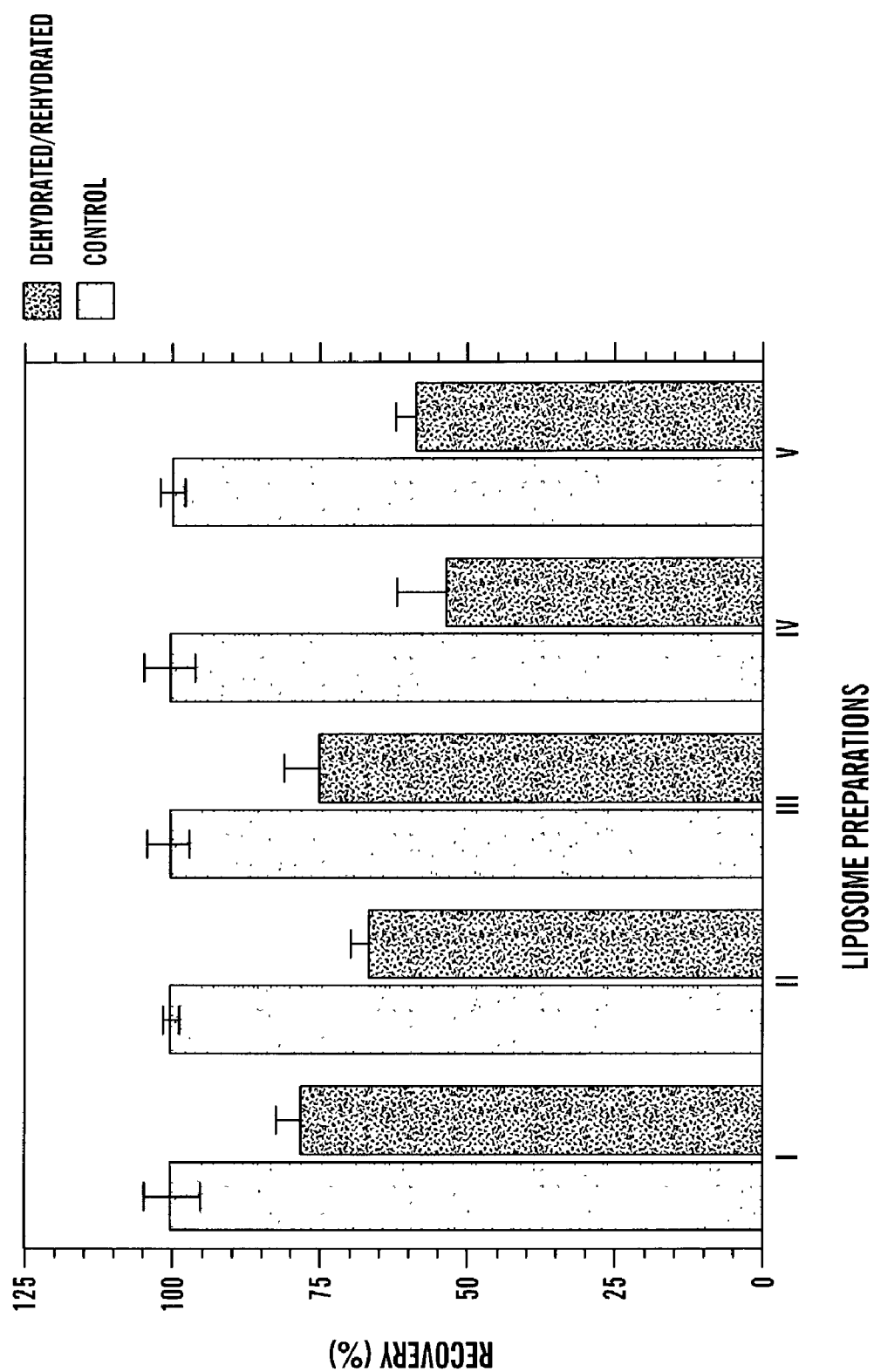
FIG. 3 is a graph showing the recovery of dehydrated liposomes with varying internal concentrations of trehalose. Nitrocellulose strips incorporating a 4.5 µg antibiotin band were used with approximately $5.3 \times 10^8$ biotin-tagged liposomes and normal human serum as the mobile phase. For the controls, each point is an average of three strips and, for the dehydrated liposomes, it is an average of four strips and one standard deviation is shown as an error bar. Internal trehalose concentrations: 0 mM (I), 10 mM (II), 50 mM (III), 100 mM (IV), and 200 mM (V).

The comparisons among liposomes batches I to V (all with the same internal osmolality of 827 mOsmol/kg) and batches VI to VIII (all with internal osmolality of 204 mOsmol/kg) in FIGS. 3 and 4 showed similar recoveries after the dehydration/rehydration process. This observation makes possible the application of this approach to a wide range of liposomes encapsulating different markers, since every water-soluble compound to be encapsulated as a marker will have its own osmolality value. This would also be of potential importance for development of a multi-analyte assay.

Example 16

Optimization of Components for Maximal Recovery of Dehydrated Liposomes

Figure 6:
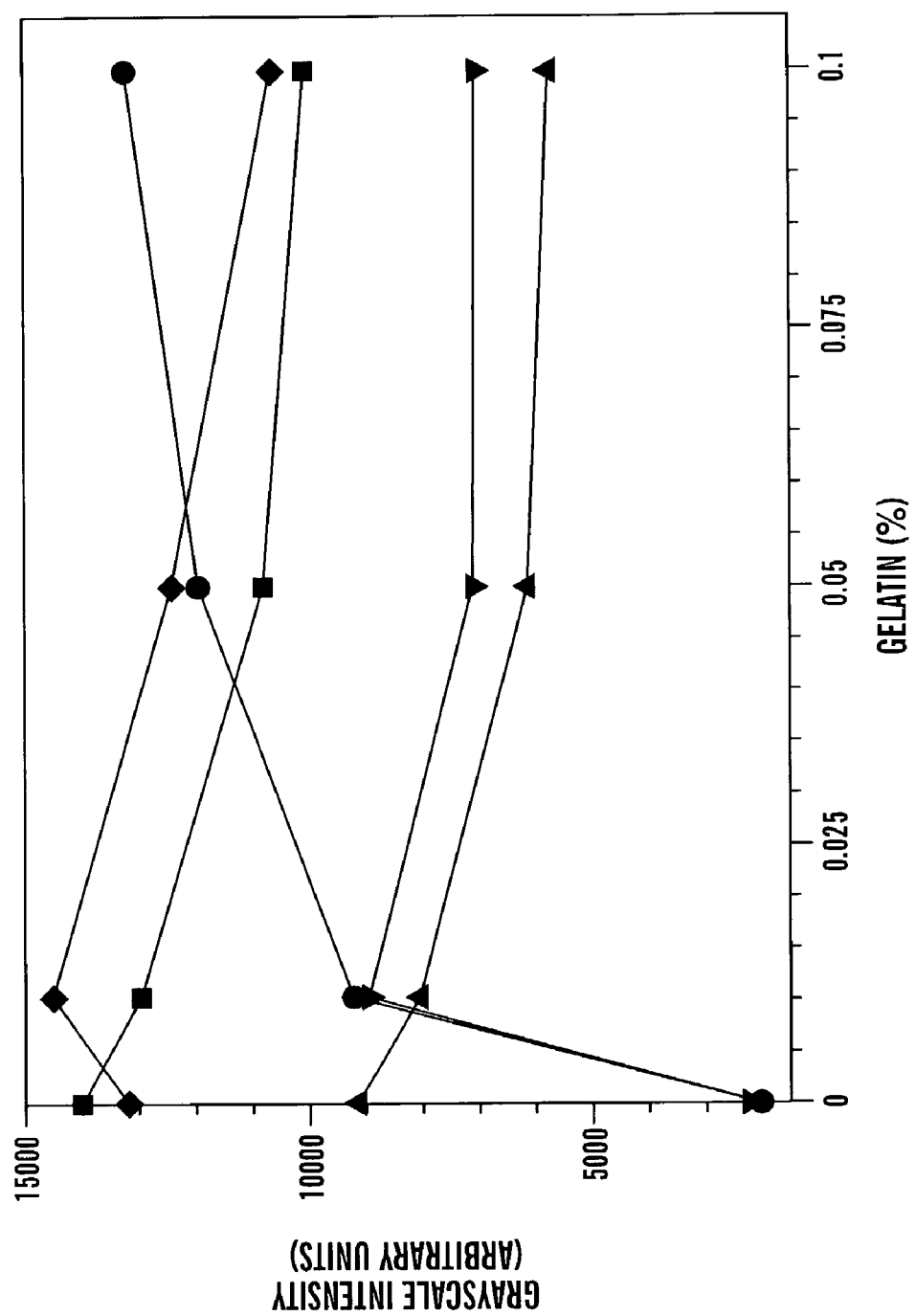
FIG. 6 is a graph showing the effect of gelatin and polyvinylpyrrolidone (PVP) concentrations in blocking reagent on the recovery of dehydrated liposomes and the nitrocellulose strips expressed as signal intensities of the antibiotin band produced by intact liposomes. Nitrocellulose strips incorporating a 4.5 µg antibiotin band were used with approximately $5.3 \times 10^8$ biotin-tagged liposomes and normal human serum as the mobile phase. PVP concentrations: 0% (●), 0.05% (■), 0.2% (♦), 0.5% (▲), and 1% (▼).

The observation that external sugar was necessary for the preservation of the dehydrated liposomes necessitated a redetermination of the optimal concentrations of the blocking agents needed for maximal recovery of the dehydrated sucrose-enriched liposomes. Experiments using PVP and gelatin by themselves or mixed in different proportions were performed using liposome batch I (no internal trehalose) enriched with 0.44 M sucrose in the diluent (0.44 M was used before 0.7 to 1.0 M was determined to be the optimal range). FIG. 6 shows the effects of combinations of PVP and gelatin on the recovery of the dehydrated liposomes. Gelatin by itself is able to preserve a large number of liposomes, but the uniformity over the capture zone is poor. The results indicate that the membranes blocked with 0.2% PVP and 0.01% gelatin provided the highest recovery of the dehydrated/rehydrated liposomes. Later experiments showed no significant difference between 0.1 and 0.2% PVP when used with 0.01% gelatin. PVP was observed to be essential in providing the best flow rate and homogeneity over the antibiotin band.

Based on the foregoing observations, for best results, liposomes with diameters smaller than 384 nm and without internal sugars were made up in diluent containing between 0.7 and 1 M sucrose prior to application onto an area below the antibody band on the nitrocellulose strips blocked with 0.1 or 0.2% PVP and 0.01% gelatin in TBS.

Example 17

Test Performance

Table 2 shows the reproducibility of the test with strips that contained dehydrated liposomes together with control strips (liposomes freshly applied) using PBS or normal human serum (NHS) as the carrier.

TABLE 2

| | Test Performance | | | |
|---|---|---|---|---|
| | Mobile phase | | | |
| | PBS | | NHS | |
| Strips | Control | De/rehydrated | Control | De/rehydrated |
| Mean recovery (%) | 100 | 71.9 | 100 | 79.6 |
| Standard deviation (%) | 6.0 | 5.0 | 7.2 | 6.8 |
| Coefficient of Variation (%) | 6.0 | 7.0 | 7.2 | 8.6 |
| N | 21 | 26 | 26 | 25 |

The percentage of recovery for strips with dehydrated liposomes is the average of the intensities of the antibiotin band of all the test strips in comparison to the intensity of the antibiotin band of the controls. Using NHS as the carrier, the recovery was significantly higher than with PBS. From these results, a range of 70 to 80% recovery was established with an acceptable coefficient of variation (CV) of $\leq 8\%$. The analysis time, which consisted of the time from the contact of the test strip containing the dehydrated liposomes with the sample solution until the solution reached the end of the strip, was less than 6 minutes. Additional time for the colorimetric quantitation with the scanner, the technique used in the laboratory, was needed. For a simpler and more user-friendly approach, a meter to measure the color intensity at a specific wavelength based on reflectometry could be used. Most simply, a visual estimation of the color intensity, using appropriate calibrants or a color intensity chart, would obviate the need for any instrumentation.

Example 18

Biotin Strip Immunoassay

Figure 7:
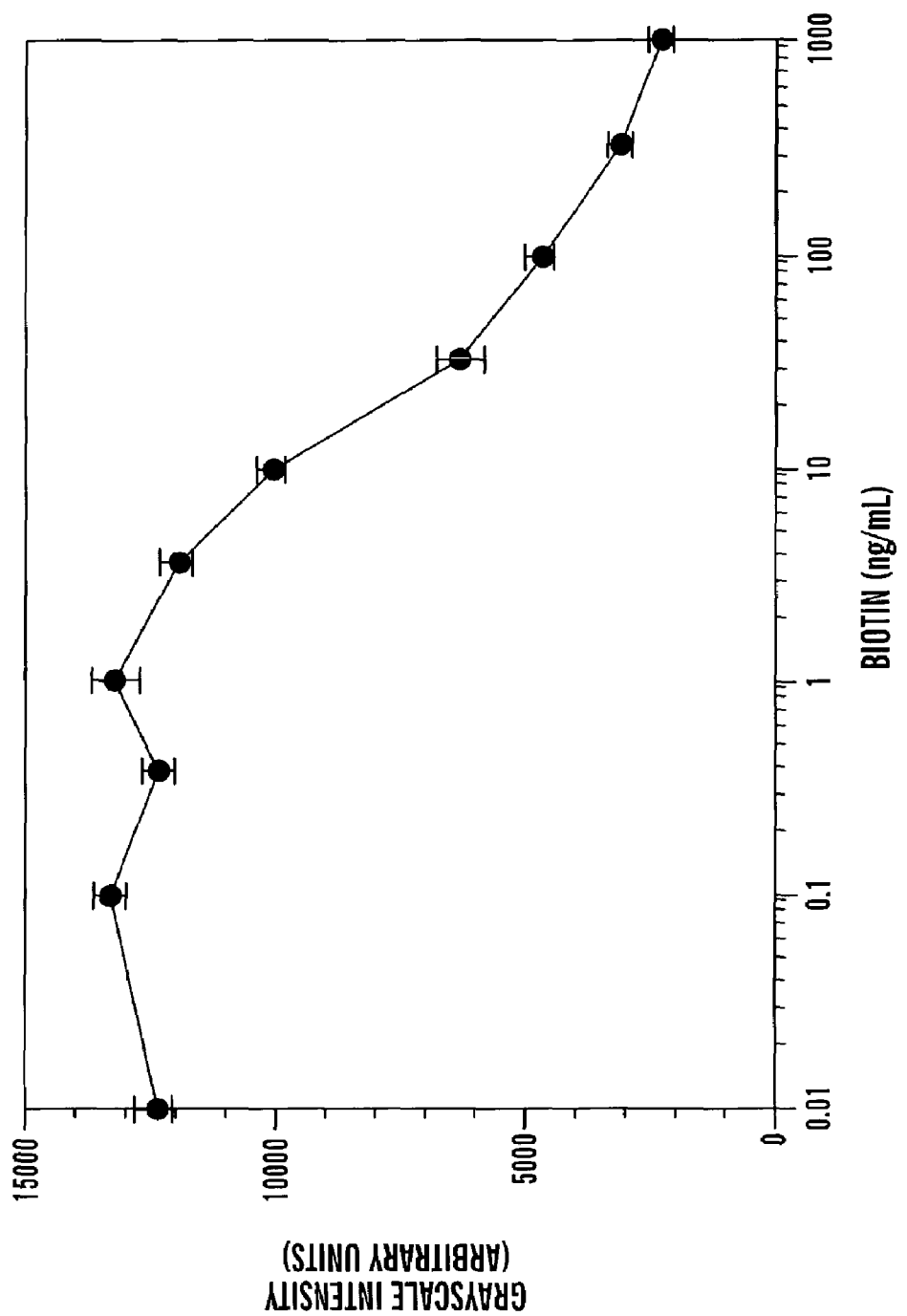
FIG. 7 is a dose-response curve for biotin. Nitrocellulose strips incorporating a 4.5 µg antibiotin band and dehydrated liposomes (approximately $5.3 \times 10^8$ biotin-tagged liposomes/strip) at a point 6 mm below the antibiotin band were used with biotin in normal human serum as test sample. Each point is an average of at least three strips, and one standard deviation is shown as an error bar.

The test was based on the principle of a competitive immunoassay. As the liquid sample migrated up the test strip, it rehydrated the dried biotin-tagged, SRB-loaded liposomes and continued to migrate toward the immobilized antibody zone, where competition occurred between the biotin-conjugated liposomes and the analyte in the sample for binding sites on the antibody. More liposomes will bind to the antibiotin zone when there is less biotin in the sample, thus, the intensity of the color on the antibody capture zone varies inversely as the concentration of the biotin in the sample. A dose-response curve for biotin in normal human serum in shown FIG. 7. This dose-response curve exhibits the sigmoidal shape of competitive immunoassays. From this curve, the limit of detection was determined to be 6 ng/mL (24.6 nM) of biotin with greater than 95% confidence. While this concentration is greater than the clinically relevant level in blood/serum, it is expected that further improvements will lower the detection limit to the requisite level.

To determine if different amounts of binding protein (antibody) on the strip would affect the limit of detection and the working range of the assay, strips were coated with 1, 2.5, and 4.5 µg of antibiotin. The strips with only 1 µg of antibiotin did not have enough antibody to bind liposomes to give a visually discernible band. The response curves obtained using strips containing 2.5 and 4.5 µg of antibiotin showed the same detection limit, but a slight improvement in the working range was observed with the higher concentration of antibiotin on the strip.

Example 19

Stability Over Time of Test Strips Containing Dehydrated Liposomes

Figure 8:
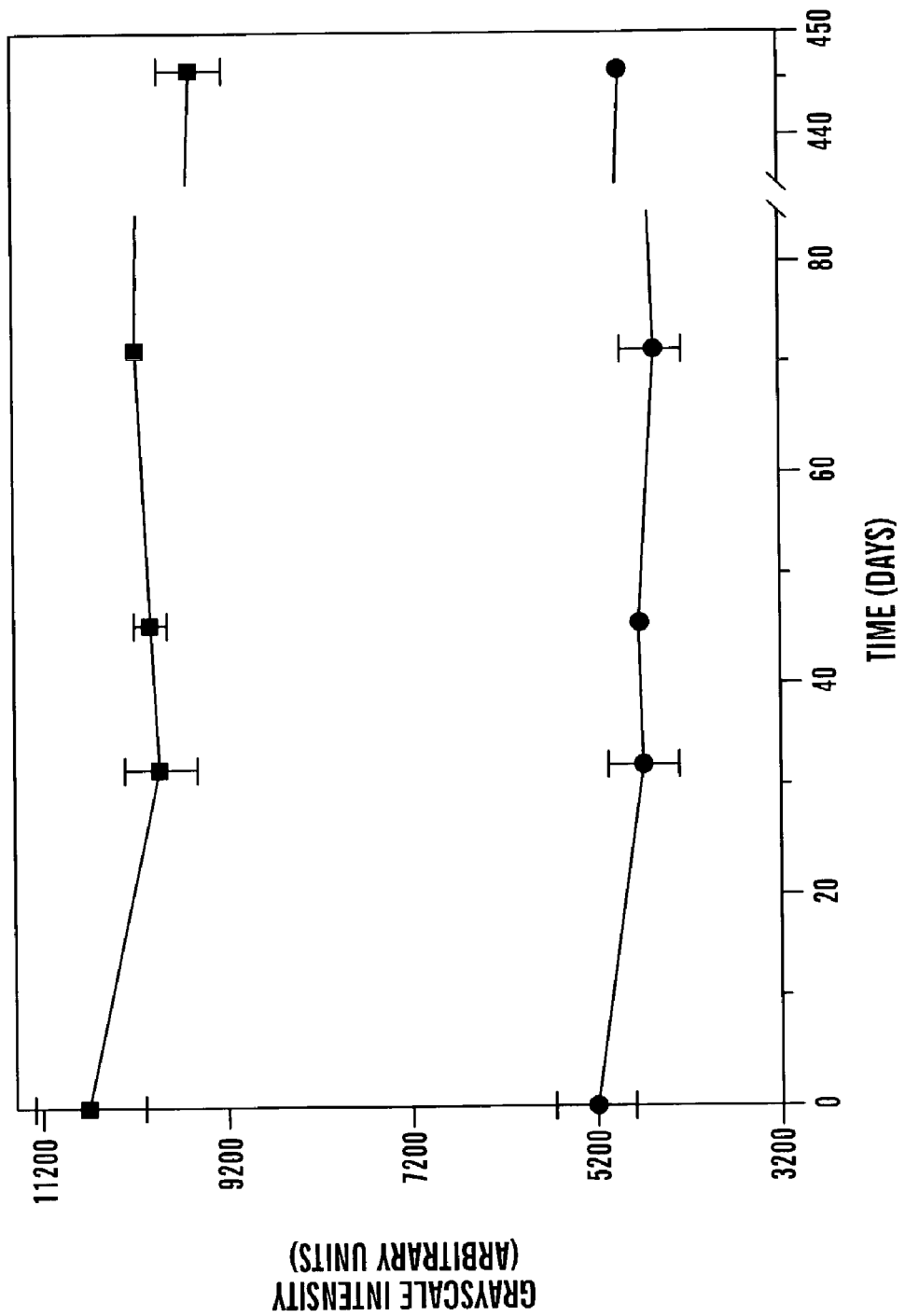
FIG. 8 is a graph showing the stability of liposomes dehydrated on nitrocellulose strips based on the signal intensities obtained over time for two concentrations of biotin: 10 ng/ml (■) and 100 ng/ml (●). Nitrocellulose strips incorporating a 4.5 µg antibiotin band and dehydrated liposomes (approximately $5.3 \times 10^8$ biotin-tagged liposomes/strip) at a point 6 mm below the antibiotin band were used with biotin in normal human serum as test sample. Each point is an average of two strips, and one standard deviation is shown as an error bar.

The strips with dehydrated liposomes were stored in vacuum-sealed plastic bag at 4° C. and protected from light. A calibration curve using strips that had been kept at 4° C. and protected from light for a year showed identical response to that obtained when the strips were freshly prepared. The results obtained with two biotin standards, 10 and 100 μg/mL biotin, tested over a period of 1.2 years using the stored test strips, are shown in FIG. 8. The insignificant change in the responses obtained for the standards indicated that the dehydrated liposomes on the NC strips were stable for at least one year. For the 10 and 100 μg/L biotin standards, the % CV values obtained are 5.50 (n=8) and 5.14 (n=7), respectively.

Thus, the feasibility of developing a rapid one-step strip immunoassay using dehydrated liposomes was demonstrated. This technique provides a simple and convenient format for point-of-care and field assay devices. The dehydration of dye-loaded liposomes in the presence of a high concentration of external sugar on a nitrocellulose membrane blocked with PVP and gelatin provided 70-80% recovery of the liposomes upon rehydration by the sample solution. The optimal external sucrose concentration was determined to be 0.7-1.0 M. Relatively large variability in liposome size, internal osmolality, encapsulant concentration, and liposome number did not affect the recovery of the liposomes, which greatly simplified the production process for the assay. The blocking conditions disclosed herein are the optimum achieved for biotin as the analyte, but modifications would be necessary for other analytes, especially proteins.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method for making a test device for detecting or quantifying an analyte in a sample comprising:
    providing a membrane with a sugar glaze on its outer surface,
    contacting the sugar glazed membrane with a mixture comprising derivatized, marker-loaded liposomes,
    substantially dehydrating the mixture on the membrane under vacuum pressure at a temperature of from about 4° C. to about 80° C., and
    immobilizing a first binding material specific for the analyte in a capture zone on the membrane.

2. The method according to claim 1, wherein the derivatized, marker-loaded liposomes are derivatized with an analyte analog.

3. The method according to claim 1, wherein the marker is a fluorescent dye, a visible dye, a bioluminescent material, a chemiluminescent material, an enzymatic substrate, a radioactive material, or an electrochemical marker.

4. The method according to claim 1, wherein the membrane is an absorbent material.

5. The method according to claim 4, wherein the absorbent material is nitrocellulose, glass fiber, woven fabric, nylon, nonwoven material, polyester fabric, rayon, cellulose rayon blend, mixed fiber of cellulose and glass, or polyethersulfone.

6. The method according to claim 1, further comprising:
    blocking the membrane in its entirety with one or more blocking agents at a concentration that prevents lysis of derivatized, marker-loaded liposomes during dehydration and rehydration.

7. The method according to claim 6, wherein the blocking agent is selected from the group consisting of polyvinylpyrrolidone, gelatin, non-fat dry milk, bovine serum albumin, casein, gum arabic, and mixtures thereof.

8. The method according to claim 1, wherein the dehydrating is carried out at a temperature of from about 4° C. to about 50° C.

9. The method according to claim 1, wherein the sugar is selected from the group consisting of sucrose, trehalose, maltose, glucose, lactose, and mixtures thereof.

10. A test device for detecting or quantifying an analyte in a sample comprising:
    a sugar glazed membrane which comprises an immobilized liposome zone, wherein the immobilized liposome zone has bound thereto dehydrated, derivatized, marker-loaded liposomes and a capture zone having a first binding material specific for the analyte bound thereto.

11. The test device according to claim 10, wherein the marker is a fluorescent dye, a visible dye, a bioluminescent material, a chemiluminescent material, an enzymatic substrate, a radioactive material, or an electrochemical marker.

12. The test device according to claim 10, wherein the membrane is an absorbent material.

13. The test device according to claim 12, wherein the absorbent material is nitrocellulose, glass fiber, woven fabric, nylon, nonwoven material, polyester fabric, rayon, cellulose rayon blend, mixed fiber of cellulose and glass, or polyethersulfone.

14. The test device according to claim 10, wherein sugar is selected from the group consisting of sucrose, trehalose, maltose, glucose, lactose, and mixtures thereof.

15. A test device according to claim 10, further comprising:
    one or more blocking agents blocking the membrane in its entirety at a concentration that prevents lysis of derivatized, marker-loaded liposomes during dehydration and rehydration.

* * * * *